United States Patent
Colley et al.

(10) Patent No.: US 10,280,155 B2
(45) Date of Patent: *May 7, 2019

(54) PROCESS FOR PREPARING 4-(4-(4-(((3R,5R)-5-((1H-1,2,4-TRIAZOL-1-YL)METHYL)-5-(2,4-DIFLUORO-PHENYL)TETRAHYDROFURAN-3-YL)METHOXY)-3-METHYLPHENYL)PIPERAZIN-1-YL)-N-((1S,2S)-2-HYDROXYCYCLOHEXYL) BENZAMIDE OR A PHARMACEUTICALLY ACCEPTABLE SALT THEREOF

(71) Applicant: PULMOCIDE LIMITED, London (GB)

(72) Inventors: Thomas Christopher Colley, London (GB); Kazuhiro Ito, London (GB); Peter Strong, London (GB); Mihiro Sunose, Nottingham (GB); Matthew McConville, Nottingham (GB)

(73) Assignee: PULMOCIDE LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/971,316

(22) Filed: May 4, 2018

(65) Prior Publication Data

US 2018/0251453 A1    Sep. 6, 2018

Related U.S. Application Data

(63) Continuation of application No. 15/347,402, filed on Nov. 9, 2016, now Pat. No. 9,969,720, which is a continuation-in-part of application No. PCT/GB2016/051467, filed on May 20, 2016.

(30) Foreign Application Priority Data

May 21, 2015  (EP) ..................... 15168637

(51) Int. Cl.
  *C07D 405/06*  (2006.01)
  *A61K 31/496*  (2006.01)
  *A61K 45/06*  (2006.01)

(52) U.S. Cl.
  CPC .......... *C07D 405/06* (2013.01); *A61K 31/496* (2013.01); *A61K 45/06* (2013.01)

(58) Field of Classification Search
  CPC .................................. C07D 405/06
  See application file for complete search history.

(56) References Cited

U.S. PATENT DOCUMENTS

| | | |
|---|---|---|
| 5,039,676 A | 8/1991 | Saksena et al. |
| 5,486,625 A | 1/1996 | Leong et al. |
| 5,714,490 A | 2/1998 | Saksena et al. |

| | | |
|---|---|---|
| 2017/0037035 A1 | 2/2017 | Sunose et al. |
| 2017/0320858 A1 | 11/2017 | Colley et al. |

FOREIGN PATENT DOCUMENTS

| | | |
|---|---|---|
| EP | 0228125 B1 | 3/1992 |
| EP | 0957101 A1 | 11/1999 |
| WO | 89/04829 A1 | 6/1989 |
| WO | 95/17407 A1 | 6/1995 |
| WO | 96/38443 A1 | 12/1996 |
| WO | 02/080678 A1 | 10/2002 |
| WO | 2013/036866 A1 | 3/2013 |

(Continued)

OTHER PUBLICATIONS

Hepperle, et al.—Tetrahedron Letters 43 (2002) 18: 3359-3363—"Mono N-arylation of piperazine(III): metal-catalyzed N-arylation and its application . . . . "

(Continued)

*Primary Examiner* — Emily A Bernhardt
(74) *Attorney, Agent, or Firm* — Birch, Stewart, Kolasch & Birch, LLP

(57) ABSTRACT

A process for preparing a compound of formula (I):

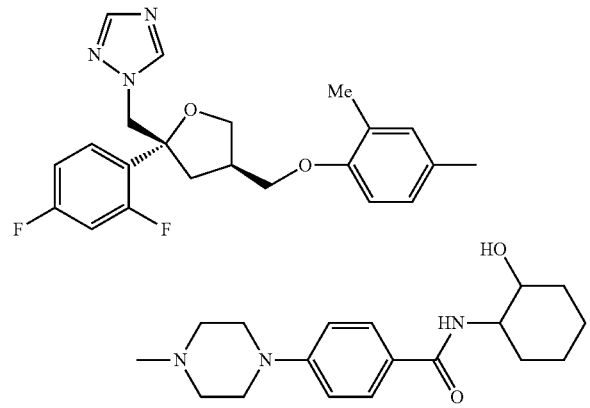

or a pharmaceutically acceptable salt thereof includes reacting a compound of formula (6):

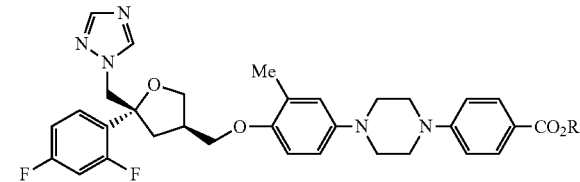

(wherein R is H) with 2-aminocyclohexanol or a salt thereof.

3 Claims, 1 Drawing Sheet

Specification includes a Sequence Listing.

(56) References Cited

FOREIGN PATENT DOCUMENTS

| WO | 2016087878 A1 | 6/2016 |
| WO | 2016087880 A1 | 6/2016 |

OTHER PUBLICATIONS

Saksena, et al.—Tetrahedron Letters 45 (2004) 44: 8249-8251—"Stereoselective Grignard additions to N-formyl hydrazone: a concise synthesis of . . . . "

Bowyer, et al.—Pest Management Science 70 (2014) 2: 173-178—"Environmental fungicides and triazole resistance in Aspergillus".

Zacchino, et al.—Expert Opinion Ther. Patents (2014) 24(3) 323-338—Novel antifungal agents: a patent review (2011-present).

Gregson, et al.—Antimicrobial Agents and Chem. (2013) 57 (11) 5778-5780—In Vitro Susceptibility of Aspergillus fumigatus . . . .

Pfaller, et al—J. of Clin. Microbiology (2009) 47 (10) 3142-3146—"Wild-Type MIC Distribution and Epidemiological Cutoff Values for Aspergillus fumigatus . . . . "

Colley et al; Antimicrob. Agents and Chem., (2018) 62(5), 1-18—"In Vitro and In Vivo Efficacy of a Novel and Long-Acting Fungicidal Azole, PC1244, on Aspergillus fumigatus Infection".

PROCESS FOR PREPARING 4-(4-(4-(((3R,5R)-5-((1H-1,2,4-TRIAZOL-1-YL)METHYL)-5-(2,4-DIFLUORO-PHENYL)TETRAHYDROFURAN-3-YL)METHOXY)-3-METHYLPHENYL)PIPERAZIN-1-YL)-N-((1S,2S)-2-HYDROXYCYCLOHEXYL)BENZAMIDE OR A PHARMACEUTICALLY ACCEPTABLE SALT THEREOF

CROSS REFERENCE TO RELATED APPLICATIONS

The present application is a Continuation of co-pending U.S. Non-provisional application Ser. No. 15/347,402, filed Nov. 9, 2016, which in turn, is a Continuation-In-Part claiming priority from PCT Application No. PCT/GB2016/051467, filed May 20, 2016, which in turn, claims priority from European Application No. 15168637.5, filed May 21, 2015. Applicants claim the benefits of 35 U.S.C. § 120 as to the Non-provisional U.S. applications and the PCT application, and priority under 35 U.S.C. § 119 as to the said European application, and the entire disclosures of all applications are incorporated herein by reference in their entireties.

FIELD OF THE INVENTION

This invention relates to compounds useful in the treatment of mycoses, compositions containing it and its use in therapy.

BACKGROUND OF THE INVENTION

The incidence of fungal infections has increased substantially over the past two decades and invasive forms are leading causes of morbidity and mortality, especially amongst immunocompromised or immunosuppressed patients. Disseminated candidiasis, pulmonary aspergillosis, and emerging opportunistic fungi are the most common agents producing these serious mycoses. It is a particular feature of fungi that they are able to generate an extracellular matrix (ECM) that binds them together and allows them to adhere to their in vitro or in vivo substrates. These biofilms serve to protect them against the hostile environments of the host immune system and to resist antimicrobial killing (Kaur and Singh, 2013).

Pulmonary aspergillosis can be segmented into those patients suffering with non-invasive disease versus those with an invasive condition. A further sub-division is used to characterise patients who exhibit an allergic component to aspergillosis (known as ABPA; allergic bronchopulmonary aspergillosis) compared with those that do not. The factors precipitating pulmonary aspergillosis may be acute, such as exposure to high doses of immuno-suppressive medicines or to intubation in an intensive care unit. Alternatively, they may be chronic, such as a previous tuberculosis (TB) infection (Denning et al., 2011a). Chronic lung infections with *Aspergillus* can leave patients with extensive and permanent lung damage, requiring lifetime treatment with oral azole drugs (Limper et al., 2011).

A growing body of research suggests that *Aspergillus* infection may play an important role in clinical asthma (Chishimba et al., 2012; Pasqualotto et al., 2009). Furthermore, recently published work has correlated *Aspergillus* infection with poorer clinical outcomes in patients with chronic obstructive pulmonary disease (COPD) (Bafadhel et al., 2013). Similarly cross-sectional studies have shown associations between the presence of *Aspergillus* spp. and *Candida* spp. in the sputum and worsened lung function (Chotirmall et al., 2010; Agbetile et al., 2012).

Invasive aspergillosis (IA) exhibits high mortality rates in immunocompromised patients, for example, those undergoing allogenic stem cell transplantation or solid organ transplants (such as lung transplants). The first case of IA reported in an immunocompromised patient occurred in 1953. This event was concurrent with the introduction of corticosteroids and cytotoxic chemotherapy into treatment regimens (Rankin, 1953). Invasive aspergillosis is a major concern in the treatment of leukaemia and other haematological malignancies given its high incidence and associated mortality. Death rates usually exceed 50% (Lin et al., 2001) and long term rates can reach 90% in allogeneic hematopoietic stem cell transplantation recipients, despite the availability of oral triazole medicines (Salmeron et al., 2012). In patients undergoing solid organ transplantation (particularly of the lung), the use of high doses of steroids leaves patients vulnerable to infection (Thompson and Patterson, 2008) which is a serious problem. The disease has also appeared in less severely immunocompromised patient populations. These include those suffering with underlying COPD or cirrhosis, patients receiving high dose steroids, and individuals fitted with central venous catheters or supported by mechanical ventilation (Dimopoulos et al., 2012).

Existing anti-fungal medicines are predominantly dosed either orally or systemically. These commonly exploited routes of delivery are poor for treating lung airways infections, since drug concentrations achieved at the site of infection tend to be lower than those in organs. This is especially so for the liver, which is a site of toxicity: up to 15% of patients treated with voriconazole suffer raised transaminase levels (Levin et al., 2007; Lat and Thompson, 2011). Exposure of the liver also results in significant drug interactions arising from the inhibition of hepatic P450 enzymes (Jeong, et al., 2009; Wexler et al., 2004).

Furthermore, the widespread use of triazoles, both in the clinic and in agriculture has led to a growing and problematic emergence of resistant mycoses in some locations (Denning et al., 2011b; Bowyer and Denning, 2014).

It is clearly evident that an urgent medical need exists for novel anti-fungal medicines that deliver improved efficacy and better systemic tolerability profiles.

SUMMARY OF THE INVENTION

In a first aspect, the invention provides compound (I)

Compound (I)

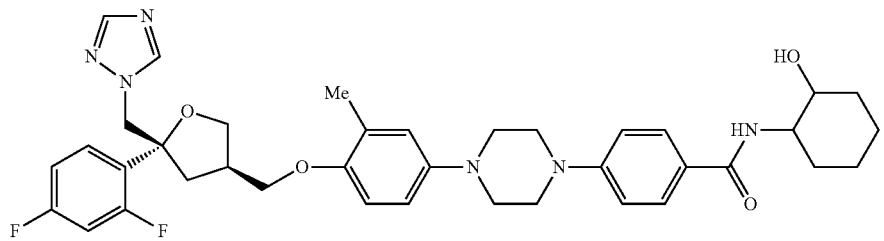

that is:

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(2-hydroxycyclohexyl)benzamide, or a pharmaceutically acceptable salt thereof (the "compound of the invention").

Compound (I) contains two stereogenic centres within the 2-aminocyclohexanol radical and is provided in the form of any of its four possible stereoisomers, either as a singular stereoisomer or as a mixture of stereoisomers in any ratio (including racemic mixtures).

In a preferred aspect, the invention provides Compound (I) in the form of a stereoisomer selected from Compounds (Ia) and (Ib) illustrated below, which are the two stereoisomers derived from the enantiomers of trans-2-aminocyclohexanol, and pharmaceutically acceptable salts thereof:

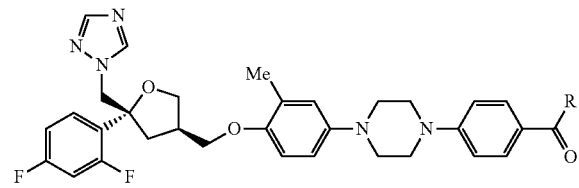

| R | Compound |
|---|---|

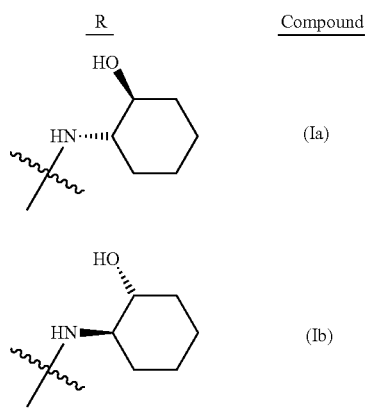

In a more preferred aspect the invention provides Compound (Ia) depicted below:

that is:

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-((1S,2S)-2-hydroxycyclohexyl) benzamide, or a pharmaceutically acceptable salt thereof.

Suitably, Compound (I) such as Compound (Ia) is provided as a singular stereoisomer. Also of interest is Compound (Ib) as a singular stereoisomer.

Biological data disclosed herein below reveals that Compound (I), and its stereoisomer Compound (Ia) in particular, are potent inhibitors of *Aspergillus fumigatus* growth in in vitro assays. In immunosuppressed mice, Compound (Ia) demonstrated potent inhibition of *Aspergillus fumigatus* infections.

DETAILED DESCRIPTION OF THE INVENTION

Figure 1:
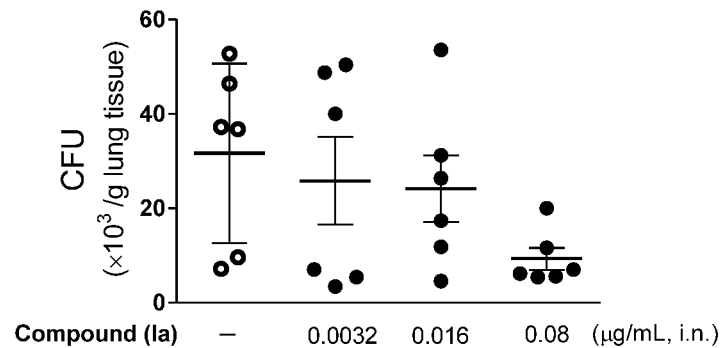
FIG. 1 displays the effects of therapeutic treatment with Compound (Ia) on CFU in the lungs of *Aspergillus fumigatus* infected, immuno-compromised, neutropenic mice.

The compound of the invention may be prepared from commercially available starting materials by the synthetic methodology depicted below (Scheme 1). Buchwald coupling of a suitably protected piperazine derivative with 4-bromo-2-methylphenol under conditions typically employed for such reactions provides the N-arylated product 1. A suitable amine protective group (P) for such transformations is a urethane group such as a Boc group (P=CO$_2{}^t$Bu). Those skilled in the art will appreciate that a wide variety of conditions may be used for affecting transformations of this kind. In particular, palladium catalysts and phosphine ligands such as RuPhosG3 and RuPhos are routinely employed in the presence of a base, for example, cesium carbonate or lithium hexamethyldisilazide.

Compound (Ia)

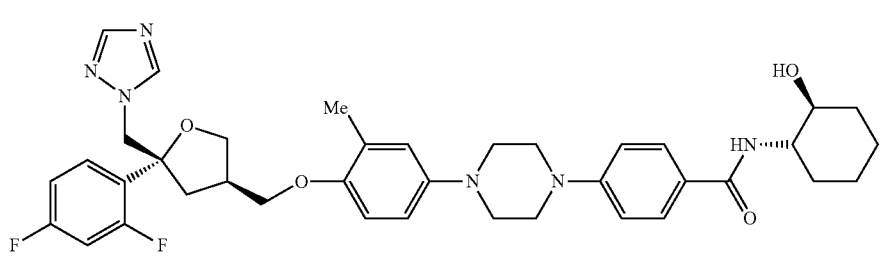

Scheme 1

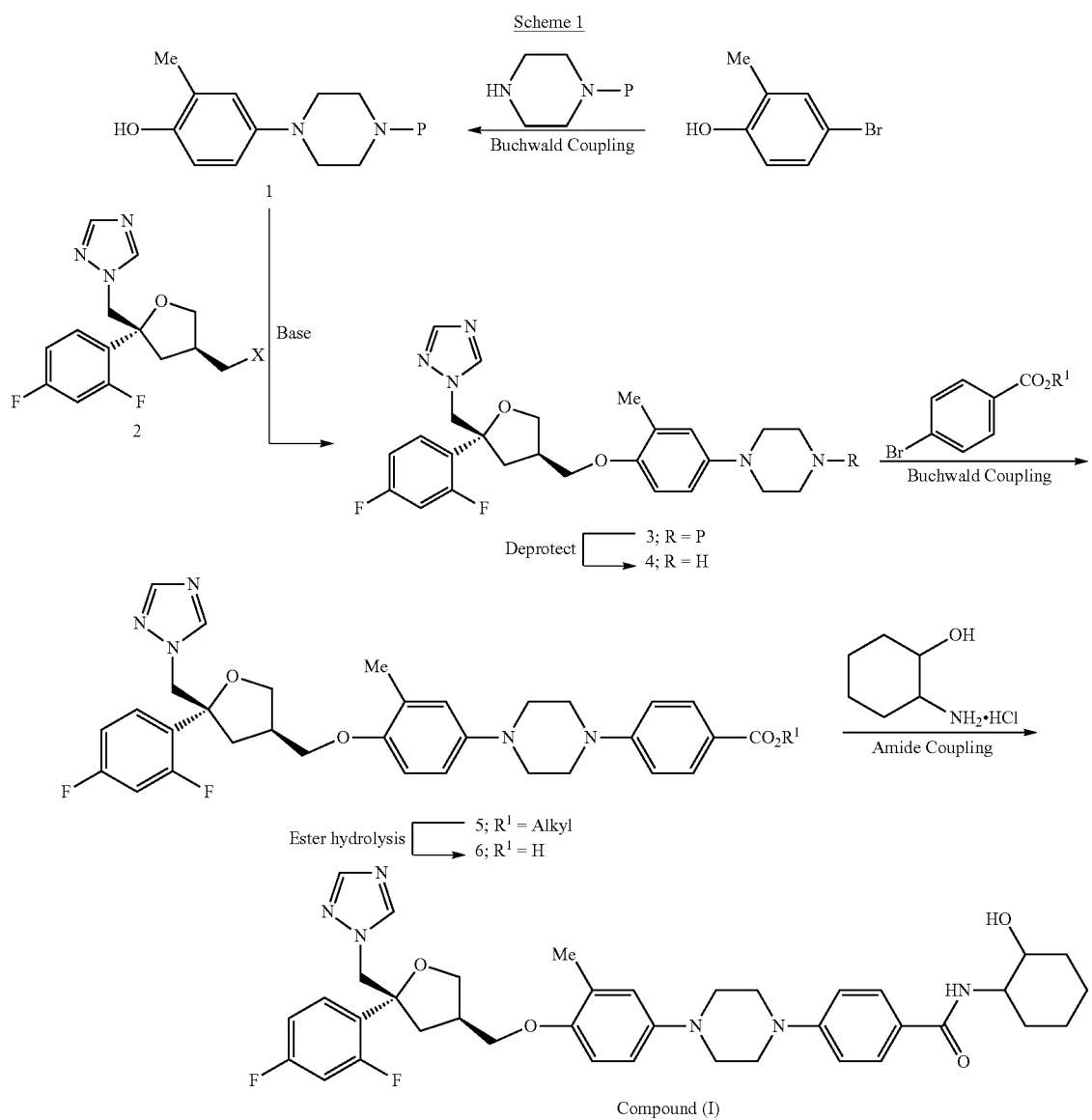

Reaction of the resulting phenol 1 with an appropriate electrophilic derivative of ((3R,5R)-5-((1H-1,2,4-triazol-1-yl)methyl)-5-(2,4-difluorophenyl)tetrahydrofuran-3-yl)methanol (2, X=OH) under basic conditions generates the ether 3. An example of such a compound is the corresponding tosylate (2, X=OTs) which is readily available, in high enantiomeric purity, from commercial sources. Whilst tosylate is exemplary, X may also be an alternative leaving group, such as a halogen, typically chlorine. Selective removal of the amine protective group reveals the monosubstituted piperazine 4. In the case of a Boc derivative (R=CO$_2^t$Bu), the deprotection step is typically undertaken by exposure of the carbamate to strong mineral acid or a strong organic acid, such as TFA, either neat or in the presence of a solvent, such as DCM.

A second Buchwald coupling of the amine 4 with an alkyl 4-bromobenzoate under basic conditions and the agency of a catalyst gives rise to the N,N'-bisarylated product 5 in which R' represents lower alkyl such as C$_{1-5}$ alkyl e.g. methyl or ethyl. Saponification of the ester 5 is conveniently undertaken by treatment with a base, such an alkali metal hydroxide, in a mixture of water and a suitable aqueous miscible solvent. Reaction of the acid product 6, with 2-aminocyclohexanol, under standard amide coupling conditions, widely available in the art, provides Compound (I). Each of the four separate stereoisomers of Compound (I) may be produced by using the corresponding single stereoisomer of 2-aminocyclohexanol. The corresponding stereoisomers of 2-aminocyclohexanol are each commercially available with high stereoisomeric purity.

Protective groups and the means for their removal are described in "Protective Groups in Organic Synthesis", by Theodora W. Greene and Peter G. M. Wuts, published by John Wiley & Sons Inc; 4th Rev Ed., 2006, ISBN-10: 0471697540. A review of methodologies for the preparation of amides is covered in: 'Amide bond formation and peptide coupling' Montalbetti, C. A. G. N. and Falque, V. *Tetrahedron*, 2005, 61, 10827-10852.

Pharmaceutically acceptable salts of compounds of formula (I) include in particular pharmaceutically acceptable acid addition salts of said compounds. The pharmaceutically acceptable acid addition salts of compounds of formula (I) are meant to comprise the therapeutically active non-toxic acid addition salts that the compounds of formula (I) are able to form. These pharmaceutically acceptable acid addition salts can conveniently be obtained by treating the free base form with such appropriate acids in a suitable solvent or mixture of solvents. Appropriate acids comprise, for example, inorganic acids such as hydrohalic acids, e.g. hydrochloric or hydrobromic acid, sulfuric, nitric, phosphoric acids and the like; or organic acids such as, for example, acetic, propanoic, hydroxyacetic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic acid and the like.

Conversely said salt forms can be converted by treatment with an appropriate base into the free base form.

The definition of Compound (I) is intended to include all tautomers of said compound.

As the term is used herein, a "singular stereoisomer" of Compound (I) is a stereoisomer provided in a form of both high diastereomeric and high enantiomeric purity, that is substantially free of the other three stereoisomers of Compound (I) that arise by virtue of the presence therein of the 2-aminocyclohexanol radical. Typically, the singular stereoisomer constitutes at least 98%, 99%, 99.5%, or 99.9% w/w of the content of Compound (I) (i.e. the other stereoisomers constitutes less than 2%, 1%, 0.5%, or 0.1% w/w of the content of Compound (I).

The definition of Compound (I) is intended to include all solvates of said compound (including solvates of salts of said compound) unless the context specifically indicates otherwise. Examples of solvates include hydrates.

The compound of the disclosure includes embodiments wherein one or more atoms specified are naturally occurring or non-naturally occurring isotopes. In one embodiment the isotope is a stable isotope. Thus the compounds of the disclosure include, for example deuterium containing compounds and the like.

The disclosure also extends to all polymorphic forms of the compound herein defined.

Novel intermediates as described herein such as compounds of formula (3), (4), (5) and (6) and salts thereof, form a further aspect of the invention. Salts include pharmaceutically acceptable salts (such as those mentioned above) and non-pharmaceutically acceptable salts. Salts of acids (e.g. carboxylic acids) include first and second group metal salts including sodium, potassium, magnesium and calcium salts.

In an embodiment there is provided a pharmaceutical composition comprising the compound of the invention optionally in combination with one or more pharmaceutically acceptable diluents or carriers.

Suitably the compound of the invention is administered topically to the lung or nose, particularly, topically to the lung. Thus, in an embodiment there is provided a pharmaceutical composition comprising the compound of the invention optionally in combination with one or more topically acceptable diluents or carriers.

Suitable compositions for pulmonary or intranasal administration include powders, liquid solutions, liquid suspensions, nasal drops comprising solutions or suspensions or pressurised or non-pressurised aerosols.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). The compositions may also conveniently be administered in multiple unit dosage form.

Topical administration to the nose or lung may be achieved by use of a non-pressurised formulation such as an aqueous solution or suspension. Such formulations may be administered by means of a nebuliser e.g. one that can be hand-held and portable or for home or hospital use (i.e. non-portable). An example device is a RESPIMAT inhaler. The formulation may comprise excipients such as water, buffers, tonicity adjusting agents, pH adjusting agents, viscosity modifiers, surfactants and co-solvents (such as ethanol). Suspension liquid and aerosol formulations (whether pressurised or unpressurised) will typically contain the compound of the invention in finely divided form, for example with a $D_{50}$ of 0.5-10 µm e.g. around 1-5 µm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

According to one specific aspect of the invention there is provided a pharmaceutical composition comprising the compound of the invention in particulate form suspended in an aqueous medium. The aqueous medium typically comprises water and one or more excipients selected from buffers, tonicity adjusting agents, pH adjusting agents, viscosity modifiers and surfactants.

Topical administration to the nose or lung may also be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a dry-powder formulation. A dry powder formulation will contain the compound of the disclosure in finely divided form, typically with an MMD of 1-10 µm or a $D_{50}$ of 0.5-10 µm e.g. around 1-5 µm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument).

The formulation will typically contain a topically acceptable diluent such as lactose, glucose or mannitol (preferably lactose), usually of comparatively large particle size e.g. an MMD of 50 µm or more, e.g. 100 µm or more or a $D_{50}$ of 40-150 µm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients such as sodium stearate, calcium stearate or magnesium stearate.

A dry powder formulation is typically delivered using a dry powder inhaler (DPI) device. Example dry powder delivery systems include SPINHALER, DISKHALER, TURBOHALER, DISKUS, SKYEHALER, ACCUHALER and CLICKHALER. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

The compound of the invention is useful in the treatment of mycoses and for the prevention or treatment of disease associated with mycoses.

In an aspect of the invention there is provided use of the compound of the invention in the manufacture of a medicament for the treatment of mycoses and for the prevention or treatment of disease associated with mycoses.

In another aspect of the invention there is provided a method of treatment of a subject with a mycosis which comprises administering to said subject an effective amount of the compound of the invention.

In another aspect of the invention there is provided a method of prevention or treatment of disease associated with a mycosis in a subject which comprises administering to said subject an effective amount of the compound of the invention.

Mycoses may, in particular, be caused by *Aspergillus* spp. such as *Aspergillus fumigatus*.

A disease associated with a mycosis is, for example, pulmonary aspergillosis.

The compound of the invention may be used in a prophylactic setting by administering the said compound prior to onset of the mycosis.

In another aspect of the invention there is provided a method of treatment of a subject with an aspergilloma which comprises administering to said subject an effective amount of the compound of the invention. There is also provided a method of preventing recurrence of an aspergilloma in a subject which comprises administering to said subject an effective amount of the compound of the invention.

Subjects include human and animal subjects, especially human subjects.

The compound of the invention is especially useful for the treatment of mycoses such as *Aspergillus fumigatus* infection and for the prevention or treatment of disease associated with mycoses such as *Aspergillus fumigatus* infection in at risk subjects. At risk subjects include premature infants, children with congenital defects of the lung or heart, immunocompromised subjects (e.g. those suffering from HIV infection), asthmatics, subjects with cystic fibrosis, elderly subjects and subjects suffering from a chronic health condition affecting the heart or lung (e.g. congestive heart failure or chronic obstructive pulmonary disease).

The compound of the invention is also useful in the treatment of other mycoses (and the prevention or treatment of disease associated therewith) including those caused by *Aureobasidium pullulans, Rhizopus oryzae, Cryptococcus neoformans, Chaetomimum globosum, Penicillium chrysogenum, Fusarium graminerarum, Cladosporium herbarum, Trichophyton rubrum, Candida* spp. e.g. *Candida albicans, Candida glabrata* and *Candida krusei* and other *Aspergillus* spp. e.g. *Aspergillus flavus*.

The compound of the invention is also expected to be useful in the treatment of azole resistant mycoses (and the prevention or treatment of disease associated therewith) e.g. those caused by azole resistant *Aspergillus* spp. e.g. *Aspergillus fumigatus*.

The compound of the invention may be administered in combination with a second or further active ingredient. Second or further active ingredients may, for example, be selected from other anti-fungal agents including azole anti-fungal agents (such as voriconazole, or posaconazole), amphotericin B, an echinocandin (such as caspofungin) and an inhibitor of 3-hydroxy-3-methyl-glutaryl-CoA reductase (such as lovastatin, pravastatin or fluvastatin). Other examples of suitable azole anti-fungal agents include itraconazole and isavuconazole.

The second or further active ingredient may, for example, be selected from voriconazole, posaconazole, itraconazole and caspofungin.

Second or further active ingredients include active ingredients suitable for the treatment or prevention of a mycosis such as *Aspergillus fumigatus* infection or disease associated with a mycosis such as *Aspergillus fumigatus* infection or conditions co-morbid with a mycosis such as *Aspergillus fumigatus* infection.

The compound of the invention may be co-formulated with a second or further active ingredient or the second or further active ingredient may be formulated to be administered separately by the same or a different route.

For example, the compound of the invention may be administered to patients already being treated systemically with an anti-fungal, such as voriconazole or posaconazole or alternatively itraconazole or isavuconazole.

For example, the compound of the invention may be co-formulated with one or more agents selected from amphotericin B, an echinocandin, such as caspofungin, and an inhibitor of 3-hydroxy-3-methyl-glutaryl-CoA reductase, such as lovastatin, pravastatin or fluvastatin.

According to an aspect of the invention there is provided a kit of parts comprising (a) a pharmaceutical composition comprising the compound of the invention optionally in combination with one or more diluents or carriers; (b) a pharmaceutical composition comprising a second active ingredient optionally in combination with one or more diluents or carriers; (c) optionally one or more further pharmaceutical compositions each comprising a third or further active ingredient optionally in combination with one or more diluents or carriers; and (d) instructions for the administration of the pharmaceutical compositions to a subject in need thereof. The subject in need thereof may suffer from or be susceptible to a mycosis such as *Aspergillus fumigatus* infection.

The compound of the invention may be administered at a suitable interval, for example once per day, twice per day, three times per day or four times per day.

A suitable dose amount for a human of average weight (50-70 kg) is expected to be around 50 µg to 10 mg/day e.g. 500 µg to 5 mg/day although the precise dose to be administered may be determined by a skilled person.

The compound of the invention is expected to have one or more of the following favourable attributes:

potent antifungal activity, particularly activity against *Aspergillus* spp. such as *Aspergillus fumigates*, especially following topical administration to the lung or nose;

long duration of action in lungs, preferably consistent with once daily dosing;

low systemic exposure following topical administration to the lung or nose; and acceptable safety profile, especially following topical administration to the lung or nose.

EXPERIMENTAL SECTION

Abbreviations used herein are defined below (Table 1). Any abbreviations not defined are intended to convey their generally accepted meaning.

TABLE 1

| Abbreviations | |
|---|---|
| ABPA | allergic bronchopulmonary aspergillosis |
| aq | aqueous |
| ATCC | American Type Culture Collection |
| BALF | bronchoalveolar lavage fluid |
| BEAS2B | bronchial epithelium + adenovirus 12-SV40 hybrid, line 2B |
| Boc | tert-butyloxycarbonyl |
| br | broad |
| BSA | bovine serum albumin |
| $CC_{50}$ | 50% cell cytotoxicity concentration |
| CFU | colony forming unit(s) |
| CLSI | Clinical and Laboratory Standards Institute |
| COI | cut off index |
| conc | concentration |
| COPD | chronic obstructive pulmonary disease |
| d | doublet |
| DCM | dichloromethane |
| DMAP | 4-dimethylaminopyridine |
| DMEM | Dulbecco's Modified Eagle Medium |
| DMF | N,N-dimethylformamide |
| DMSO | dimethyl sulfoxide |
| DNA | deoxyribonucleic acid |
| DSS | dextran sodium sulphate |
| EBM | endothelial cell basal media |
| ECM | extracellular matrix |
| EDCI | 1-ethyl-3-(3-dimethylaminopropyl)carbodiimide |
| ee | enantiomeric excess |
| EGM | endothelial cell growth media |
| EUCAST | European Committee on Antimicrobial Susceptibility Testing |
| (ES⁺) | electrospray ionization, positive mode |
| EtOAc | ethyl acetate |
| FAM | 6-fluorescein amidite |
| FBS | foetal bovine serum |

TABLE 1-continued

| Abbreviations | |
|---|---|
| GM | galactomannan |
| hr | hour(s) |
| HPAEC | primary human pulmonary artery endothelial cells |
| IA | invasive aspergillosis |
| i.n. | intranasal |
| i.t. | intra-tracheal |
| LC-MS/MS | liquid chromatography-mass spectrometry |
| Li Hep | lithium heparin |
| LiHMDS | lithium bis(trimethylsilyl)amide |
| $(M + H)^+$ | protonated molecular ion |
| MDA | malondialdehyde |
| Me | methyl |
| MeCN | acetonitrile |
| MeOH | methanol |
| MHz | megahertz |
| $MIC_{50}$ | 50% of minimum inhibitory concentration |
| $MIC_{75}$ | 75% of minimum inhibitory concentration |
| $MIC_{90}$ | 90% of minimum inhibitory concentration |
| min | minute(s) |
| MMD | mass median diameter |
| MOI | multiplicity of infection |
| MOPS | 3-(N-morpholino)propanesulfonic acid |
| m/z: | mass-to-charge ratio |
| NCPF | National Collection of Pathogenic Fungi |
| NMR | nuclear magnetic resonance (spectroscopy) |
| NT | not tested |
| OD | optical density |
| PBS | phosphate buffered saline |
| PCR | polymerase chain reaction |
| P | protective group |
| q | quartet |
| RT | room temperature |
| RP HPLC | reverse phase high performance liquid chromatography |
| RPMI | Roswell Park Memorial Institute medium |
| RuPhos | 2-dicyclohexylphosphino-2',6'-diisopropoxybiphenyl |
| RuPhosG3 | (2-dicyclohexylphosphino-2',6'-diisopropoxybiphenyl)[2-(2'-amino-1,1'-biphenyl)]palladium (II)methanesulfonate |
| s | singlet |
| sat | saturated |
| sc | sub-cutaneous |
| SDS | sodium dodecyl sulphate |
| t | triplet |
| TAMRA | tetramethyl-6-carboxyrhodamine |
| TB | tuberculosis |
| TE | tris-EDTA (ethylenediaminetetraacetic acid) |
| TFA | trifluoroactic acid |
| THF | tetrahydrofuran |
| TR34/L98H | An *Aspergillus fumigatus* strain containing a leucine-to-histidine substitution at codon 98 and a 34-bp tandem repeat |
| TR46/Y121F/ T289A | An *Aspergillus fumigatus* strain containing a tyrosine-to-phenylalanine substitution at codon 121, a threonine-to-alanine substitution at codon 289 and a 46-bp tandem repeat |
| vol | volume(s) |

General Procedures

All reagents and solvents were obtained either from commercial sources or prepared according to the literature citation. Unless otherwise stated all reactions were stirred. Organic solutions were routinely dried over anhydrous magnesium sulfate.

Analytical Methods

Reverse Phase HPLC Methods:

Waters Xselect CSH C18 XP column, 2.5 μm (4.6×30 mm) at 40° C.; flow rate 2.5-4.5 mL min$^{-1}$ eluted with a H$_2$O-MeCN gradient containing either 0.1% v/v formic acid (Method 1a) or 10 mM NH$_4$HCO$_3$ in water (Method 1b) over 4 min employing UV detection at 254 nm. Gradient information: 0-3.00 min, ramped from 95% H$_2$O-5% MeCN to 5% H$_2$O-95% MeCN; 3.00-3.01 min, held at 5% H$_2$O-95% MeCN, flow rate increased to 4.5 mL min$^{-1}$; 3.01 3.50 min, held at 5% H$_2$O-95% MeCN; 3.50-3.60 min, returned to 95% H$_2$O-5% MeCN, flow rate reduced to 3.50 mL min$^{-1}$; 3.60-3.90 min, held at 95% H$_2$O-5% MeCN; 3.90-4.00 min, held at 95% H$_2$O-5% MeCN, flow rate reduced to 2.5 mL min$^{-1}$.

$^1$H NMR Spectroscopy:

$^1$H NMR spectra were acquired on a Bruker Advance III spectrometer at 400 MHz using residual undeuterated solvent as reference and unless specified otherwise were run in DMSO-d$_6$.

Preparation of Compounds (Ia-d): the Stereoisomers of Compound (I)

The syntheses of optically pure cis and trans 2-amino hexanols have been previously reported (Jacobsen et al., 1997). These materials are available in high enentiomeric purity from numerous commercial sources and were used as supplied.

Tert-butyl 4-(4-hydroxy-3-methylphenyl)piperazine-1-carboxylate

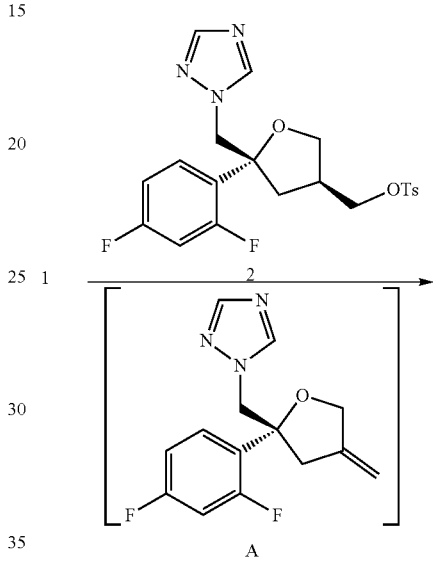

A flask charged with tert-butylpiperazin-1-carboxylate (19.1 g, 103 mmol), 4-bromo-2-methyl phenol (16.0 g, 86.0 mmol), RuPhos (798 mg, 1.71 mmol) and RuPhos G3 (1.43 g, 1.71 mmol) was evacuated and backfilled with nitrogen three times. A solution of LiHMDS (1M in THF, 257 mL, 257 mmol) was added via cannula and the reaction mixture was heated at 70° C. for 3 h. After cooling to RT the mixture was quenched by the addition of 1M aq hydrochloric acid (400 mL) at 0° C. and then neutralised with sat aq NaHCO$_3$ (400 mL). The aq layer was extracted with EtOAc (1×400 mL then 2×200 mL) and the combined organic extracts were washed with brine (500 mL) and dried. The volatiles were removed in vacuo to give a crude product which was triturated in diethyl ether:hexane (2:1) (750 mL) and collected by filtration to afford the title compound, Intermediate 1, as a pink solid (20.7 g, 76%); R$^t$ 2.07 min (Method 1b); m/z 293 (M+H)$^+$ (ES$^+$); $^1$H NMR δ: 1.41 (9H, s), 2.07 (3H, s), 2.86-2.88 (4H, m), 3.41-3.43 (4H, m), 6.58-6.66 (2H, m), 6.71 (1H, d) and 8.73 (1H, s).

1-(4-(((3R,5R)-5-((1H-1,2,4-Triazol-1-yl)methyl)-5-(2,4-difluorophenyl)tetrahydrofuran-3-yl)methoxy)-3-methylphenyl)piperazine

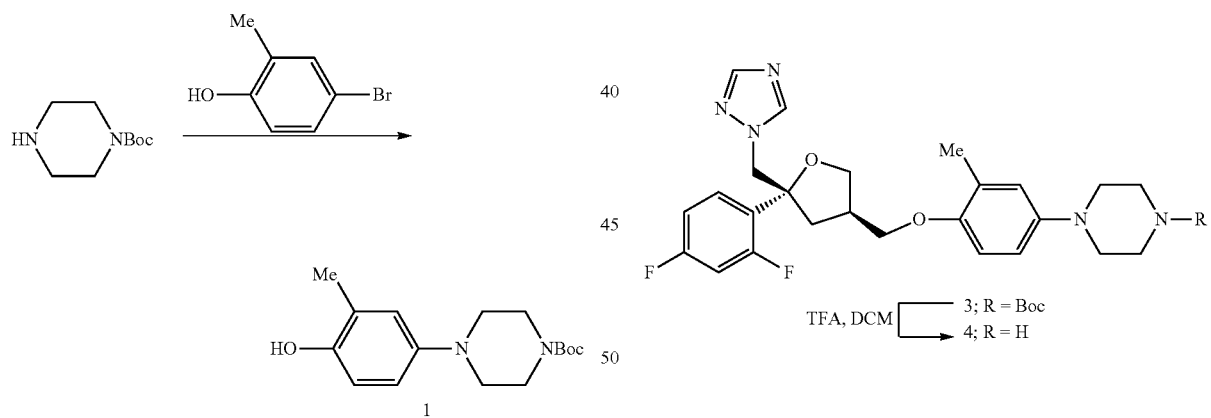

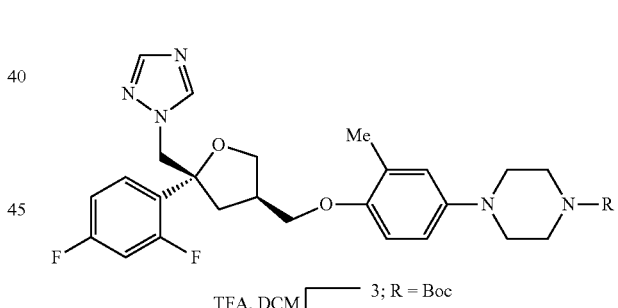

To a solution of intermediate 1 (21.5 g, 66.1 mmol) in DMSO (408 mL) was added aq sodium hydroxide (28.3 mL, 3.5 M, 99.0 mmol). The mixture was stirred at RT for 30 min and was then treated portionwise with ((3S,5R)-5-((1H-1,2,4-triazol-1-yl)methyl-5-(2,4-difluorophenyl) tetrahydrofuran-3-yl)methyl4-methylbenzenesulfonate 2 (ex API-Chem, Catalogue Number: AC-8330, 32.7 g, 72.7 mmol). The reaction mixture was stirred at 30° C. for 18 h, cooled to RT and water (600 mL) was added. The resulting mixture was extracted with EtOAc (3×500 mL) and the combined organic extracts were washed with sat aq NaHCO$_3$ (2×500 mL) and with brine (500 mL) and then dried and evaporated in vacuo to afford a brown oil (approx. 41 g). Analysis of the crude, N-Boc-protected product 3 by $^1$H NMR indicated that it contained approximately 10 mole % of the alkene elimination product: (R)-1-((2-(2,4-difluorophenyl)-4-methylenetetrahydrofuran-2-yl)methyl)-1H-1,2,4-triazole [A], together with some unreacted starting materials. This crude product was used in the subsequent step without purification.

The crude urethane 3 was taken up into DCM (260 mL) and treated with TFA (76.0 mL, 991 mmol). After 2 h at RT the reaction mixture was concentrated in vacuo to remove most of the volatiles and was then diluted with DCM (200 mL) and carefully neutralised with sat aq NaHCO$_3$ (500 mL) to pH 7, resulting in the formation of an emulsion. The mixture was acidified to pH 1 by the addition of 1M hydrochloric acid (250 mL) and DCM (350 mL) was added to form a biphasic mixture (two layers). The aq phase was separated and retained and the organic phase was extracted with 1M hydrochloric acid (800 mL). The combined aq layers were basified by the addition of 2M aq sodium hydroxide (500 mL) to pH 14 and then extracted with EtOAc (3×500 mL). The combined organic extracts were washed with brine (2000 mL) and then dried and evaporated in vacuo to afford the title compound, 4, as a viscous, brown oil (24.6 g, 78%); R$^t$ 1.46 min (Method 1a); m/z 470 (M+H)$^+$ (ES$^+$); $^1$H NMR δ: 2.07 (3H, s), 2.15 (1H, dd), 2.36-2.42 (1H, m), 2.52-2.56 (1H, m), 2.79-2.81 (4H, m), 2.87-2.90 (4H, m), 3.66 (1H, dd), 3.73-3.77 (2H, m), 4.04 (1H, t), 4.57 (2H, dd), 6.64 (1H, dd), 6.70-6.75 (2H, m), 6.99 (1H, td), 7.25-7.33 (2H, m), 7.76 (1H, s) and 8.34 (1H, s).

Methyl 4-(4-(4-(((3R,5R)-5-((1H-1,2,4-Triazol-1-yl)methyl)-5-(2,4-difluorophenyl)tetra hydrofuran-3-yl)methoxy)-3-methylphenyl)piperazin-1-yl)benzoate 6.85 (1H, br d), 7.00 (1H, td), 7.04 (2H, d), 7.27-7.34 (2H, m), 7.77 (1H, s), 7.81 (2H, d) and 8.35 (1H, s).

4-(4-(4-(((3R,5R)-5-((1H-1,2,4-Triazol-1-yl)methyl)-5-(2,4-difluorophenyl)tetrahydrofuran-3-yl)methoxy)-3-methylphenyl)piperazin-1-yl)benzoic Acid

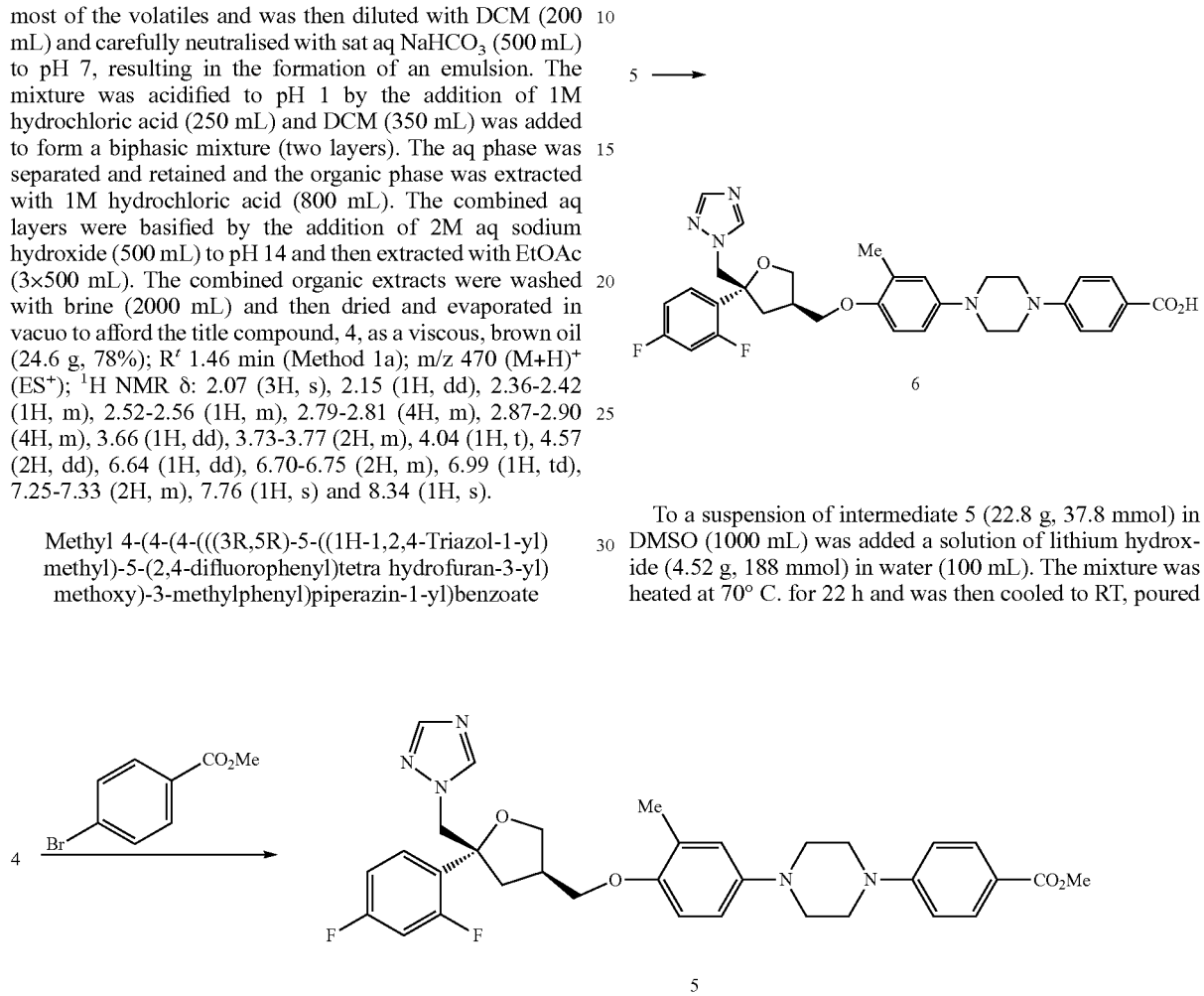

To a suspension of intermediate 5 (22.8 g, 37.8 mmol) in DMSO (1000 mL) was added a solution of lithium hydroxide (4.52 g, 188 mmol) in water (100 mL). The mixture was heated at 70° C. for 22 h and was then cooled to RT, poured A flask charged with intermediate 4 (19.1 g, 40.7 mmol), methyl-4-bromobenzoate (10.5 g, 48.8 mmol), RuPhos (0.38 g, 0.81 mmol, 2 mol %), RuPhosG3 (0.68 g, 0.81 mmol, 2 mol %) and cesium carbonate (21.2 g, 65.1 mmol) was evacuated and refilled with nitrogen three times before DMF (500 mL) was added. The mixture was heated at 90° C. for 18 h, cooled to RT and poured into water (300 mL). The resulting solid was collected by filtration and was washed with water (3×100 mL) and with diethyl ether (3×75 mL), and then dried in vacuo at 50° C. to give the title compound, 5, as a tan solid (22.8 g, 89%); R$^t$ 2.56 min (Method 1a); m/z 604 (M+H)$^+$ (ES$^+$); $^1$H NMR δ: 2.09 (3H, s), 2.16 (1H, dd), 2.36-2.42 (1H, m), 2.53-2.57 (1H, m), 3.11-3.13 (4H, m), 3.43-3.46 (4H, m), 3.67 (1H, dd), 3.74-3.79 (5H, s overlapping over m), 4.04 (1H, dd), 4.58 (2H, dd), 6.75 (2H, br s), into water (1000 mL) and acidified to pH 2 by the addition of 1M hydrochloric acid (300 mL). The mixture was cooled in an ice bath for 2 h and the resulting precipitate was collected by filtration. The filter cake was washed with water (2×200 mL) and with diethyl ether (4×200 mL). The crude solid was triturated with THF (150 mL), collected by filtration and was then washed with diethyl ether (3×100 mL) and dried in vacuo at 50° C. to give the title compound, 6 as an off-white solid (19.7 g, 88%); R$^t$ 2.28 min (Method 1a); m/z 590 (M+H)$^+$ (ES$^+$); $^1$H NMR δ: 2.09 (3H, s), 2.16 (1H, dd), 2.36-2.42 (1H, m), 2.52-2.58 (1H, m), 3.11-3.14 (4H, m), 3.41-3.44 (4H, m), 3.67 (1H, dd), 3.74-3.79 (2H, m), 4.04 (1H, dd), 4.58 (2H, dd), 6.75 (2H, br s), 6.85 (1H, br d), 6.97-7.03 (3H, m), 7.26-7.34 (2H, m), 7.77-7.80 (3H, m), 8.34 (1H, s) and 12.32 (1H, s).

Compound (1a): 4-(4-(4-(((3R,5R)-5-((1H-1,2,4-Triazol-1-yl)methyl)-5-(2,4-difluoro phenyl)tetrahydrofuran-3-yl)methoxy)-3-methylphenyl)piperazin-1-yl)-N-((1S,2S)-2-hydroxycyclohexyl)benzamide

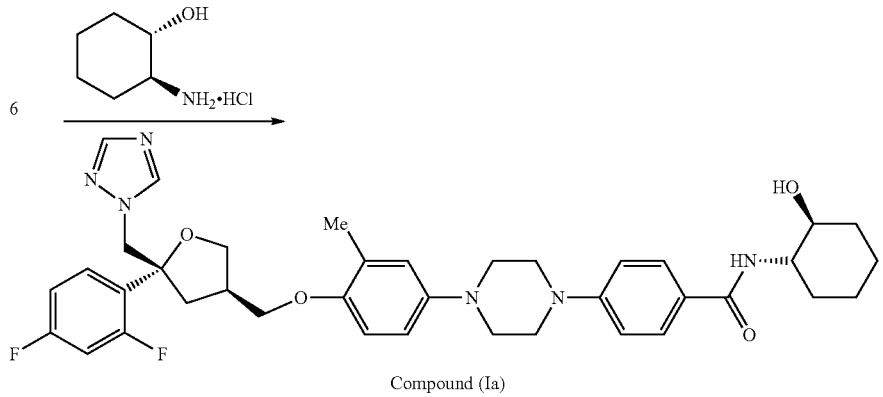

Compound (Ia)

To a mixture of intermediate 6 (100 mg, 0.17 mmol), EDCI (65 mg, 0.34 mmol) and DMAP (2.07 mg, 0.017 mmol) in pyridine (1.0 mL) was added (1S,2S)-2-aminocyclohexanol hydrochloride (51.4 mg, 0.34 mmol). The reaction mixture was stirred at RT for 16 h and was then diluted with DCM (8.0 mL) and washed with 1M hydrochloric acid (2.0 mL). The mixture was passed through a phase separator and the organics were evaporated in vacuo. The crude product so obtained was purified by flash column chromatography ($SiO_2$, 12 g, 0-5% MeOH in EtOAc, gradient elution) to afford the title compound, (Ia) as a white solid (75 mg, 64%).

Preparation of Compounds (1b-1d)

The remaining compound examples of the invention were prepared in a similar manner by coupling the benzoic acid intermediate 6 with the appropriate single stereoisomer of 2-amino cyclohexanol. These compounds are readily available from commercial sources. The materials obtained from Sigma Aldrich were supplied as the hydrochloride salts for which the following enantiopurities were specified: (1S,2S) trans isomer, >98% ee; (1R, 2R) trans isomer, >98% ee; (1R,2S) cis isomer >97% ee; (1S,2R) cis isomer, >97% ee.

The LCMS and $^1H$ NMR spectral data for compound examples (1a-1d) are presented below (Table 2).

TABLE 2

Analytical and Spectral Data for the Compounds of the Invention

| R | Example No., Name, LCMS and NMR Data |
|---|---|
| (HO, HN cyclohexyl, 1S,2S) | 1a: 4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-((1S,2S)-2-hydroxycyclohexyl) benzamide.<br>$R^1$ 2.15 min (Method 1a); m/z 687 (M + H)$^+$ (ES$^+$);<br>$^1H$ NMR δ: 1.15-1.28 (4H, m), 1.61-1.65 (2H, m), 1.82-1.92 (2H, m), 2.10 (3H, s), 2.16 (1H, dd), 2.37-2.43 (1H, m), 2.52-2.58 (1H, m), 3.12-3.15 (4H, m), 3.36-3.43 (5H, m), 3.55-3.62 (1H, m), 3.68 (1H, dd), 3.74-3.79 (2H, m), 4.05 (1H, dd), 4.53-4.62 (3H, m), 6.75 (2H, br s), 6.85 (1H, br s), 6.97-7.02 (3H, m), 7.25-7.34 (2H, m), 7.76-7.82 (4H, m), 8.34 (1H, s). |
| (HO, HN cyclohexyl, 1R,2R) | 1b: 4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-((1R,2R)-2-hydroxycyclohexyl)benzamide.<br>$R^1$ 2.14 min (Method 1a); m/z 687 (M + H)$^+$ (ES$^+$);<br>$^1H$ NMR δ: 1.15-1.28 (4H, m), 1.61-1.65 (2H, m), 1.82-1.92 (2H, m), 2.10 (3H, s), 2.16 (1H, dd), 2.37-2.43 (1H, m), 2.52-2.58 (1H, m), 3.12-3.15 (4H, m), 3.36-3.43 (5H, m), 3.55-3.62 (1H, m), 3.68 (1H, dd), 3.74-3.79 (2H, m), 4.05 (1H, dd), 4.53-4.62 (3H, m), 6.75 (2H, br s), 6.85 (1H, br s), 6.97-7.02 (3H, m), 7.25-7.34 (2H, m), 7.76-7.82 (4H, m), 8.34 (1H, s). |

TABLE 2-continued

Analytical and Spectral Data for the Compounds of the Invention

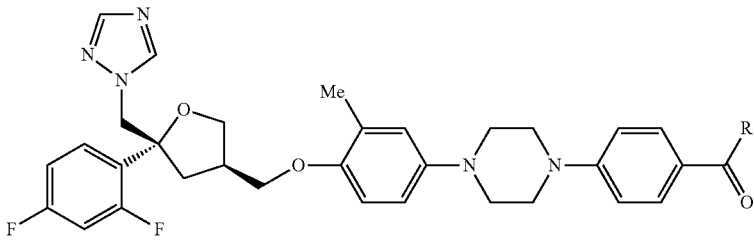

| R | Example No., Name, LCMS and NMR Data |
|---|---|
| HO,,,,,<br>HN·····<br>⌇⌇⌇ | 1c: 4-(4-(4-(((3R,5R)-5-((1H-1,2,4-triazol-1-yl)methyl)-5-(2,4-difluorophenyl)tetrahydrofuran-3-yl)methoxy)-3-methylphenyhpiperazin-1-yl)-N-((1S,2R)-2-hydroxycyclohexyl)benzamide.<br>$R^1$ 2.46 min (Method 1b); m/z 687 (M + H)$^+$ (ES$^+$);<br>$^1$H NMR δ: 1.23-1.34 (2H, m), 1.41-1.74 (6H, m), 2.10 (3H, s), 2.16 (1H, dd), 2.37-2.42 (1H, m), 2.52-2.58 (1H, m), 3.12-3.14 (4H, m), 3.36-3.38 (4H, m), 3.68 (1H, dd), 3.74-3.82 (4H, m), 4.05 (1H, dd), 4.58 (2H, dd), 4.68 (1H, d), 6.75 (2H, br s), 6.85 (1H, br s), 6.98-7.02 (3H, m), 7.26-7.34 (2H, m), 7.51 (1H, d), 7.75-7.77 (3H, m), 8.34 (1H, s). |
| HO,,,,,<br>HN⌇⌇⌇ | 1d: 4-(4-(4-(((3R,5R)-5-((1H-1,2,4-triazol-1-yl)methyl)-5-(2,4-difluorophenyl)tetrahydrofuran-3-yl)methoxy)-3-methylphenyhpiperazin-1-yl)-N-((1R,2S)-2-hydroxycyclohexyl)benzamide.<br>$R^1$ 2.46 min (Method 1b); m/z 687 (M + H)$^+$ (ES$^+$);<br>$^1$H NMR δ: 1.23-1.34 (2H, m), 1.41-1.74 (6H, m), 2.10 (3H, s), 2.16 (1H, dd), 2.37-2.42 (1H, m), 2.52-2.58 (1H, m), 3.12-3.14 (4H, m), 3.36-3.38 (4H, m), 3.68 (1H, dd), 3.74-3.82 (4H, m), 4.05 (1H, dd), 4.58 (2H, dd), 4.68 (1H, d), 6.75 (2H, br s), 6.85 (1H, br s), 6.97-7.02 (3H, m), 7.25-7.34 (2H, m), 7.50 (1H, d), 7.75-7.77 (3H, m), 8.34 (1H, s). |

Biological Testing: Experimental Methods

Assessment of Planktonic Fungus Growth: Broth Microdilution Assay

This assay was conducted using a modified method published by EUCAST (Rodriguez-Tudela, et al., 2008). Spores of *Aspergillus fumigatus* (NCPF2010, NCPF7010 [methionine 220 mutation], NCPF7099 [Glycine G54 mutation]) from Public Health England, Wiltshire; TR34/L98H mutants from St Louis Hospital, Paris, France; TR46/Y121F/T289A mutants from University of Delhi, Delhi, India) were cultured in Sabouraud dextrose agar for 3 days. A stock spore suspension was prepared from a Sabouraud dextrose agar culture by washing with PBS-tween (10 mL; phosphate buffered saline containing 0.05% Tween-20, 100 U/mL penicillin and 100 U/mL streptomycin). The spore count was assessed using a Neubauer haemocytometer and then adjusted to $10^6$ spores/mL with PBS. A working suspension of spores ($2×10^5$ spores/mL) was prepared in filter sterilised, BSA MOPS RPMI-1640 (50 mL; RPMI-1640 containing 2 mM L-glutamine, 0.5% BSA, 2% glucose, 0.165 M MOPS, buffered to pH 7 with NaOH).

For the assay, BSA MOPS RPMI-1640 (50 μL/well) was added throughout the 384-well plate (Catalogue number 353962, BD Falcon, Oxford, UK) first. Test compounds (0.5 μL DMSO solution) were then added in quadruplicate using an Integra VIAFLO 96 (Integra, Zizers, Switzerland), and mixed well using a plate mixer. Subsequently 50 μL of the working spore suspension prepared above was added to all wells except non-spore control wells. For non-spore control wells, BSA MOPS RPMI-1640 solution (50 μL/well) was added instead. The plate was covered with a plastic lid, and incubated (35° C. with ambient air) for 48 hr. The OD of each well at 530 nm was determined using a multi-scanner (Clariostar: BMG, Buckinghamshire, UK). The percentage inhibition for each well was calculated and the MIC$_{50}$, MIC$_{75}$ and MIC$_{90}$ values were calculated from the concentration-response curve generated for each test compound.

Fungus panel screening was conducted by Eurofins Panlabs Inc. The MIC and MIC$_{50}$ values of the test articles were determined following the guidelines of the CLSI: broth microdilution methods for yeast (CLSI M27-A2), (CLSI, 2002) and for filamentous fungi (CLSI M38-A), (CLSI, 2008).

*Aspergillus fumigatus* Infection of Bronchial Epithelial Cells

BEAS2B cells were seeded in 96-well plates (100 μL; $3×10^4$ cells/well; Catalogue No 3596, Sigma Aldrich, Dorset, UK) in 10% FBS RPMI-1640 and were then incubated (37° C., 5% CO$_2$) for one day before experimentation. Test compounds (0.5 μL DMSO solution) or vehicle (DMSO) were added to each well to give a final DMSO concentration of 0.5%. BEAS2B cells were incubated with test compounds for 1 hr (35° C., 5% CO$_2$) before infection with *Aspergillus fumigatus* (20 uL; Public Health England) conidia suspension ($0.5×10^5$/mL in 10% FBS RPMI-1640). The plate was incubated for 24 hr (35° C., 5% CO$_2$). Supernatant (50 uL) was collected and transferred to a PCR plate (Catalogue No L1402-9700, Starlab, Milton Keynes, UK), which was frozen (−20° C.) until use. After thawing, supernatant (5 μL) was diluted 1:20 by adding R7-PBS solution (95 μL; 1:4 R7 to PBS; Bio-Rad Laboratories, Redmond, Wash., USA). Galactomannan levels in these samples (50 μL) were measured using Platelia GM-EIA kits (Bio-Rad Laboratories, Redmond, Wash., USA). The percentage inhibition for each well was calculated and the IC$_{50}$ value was calculated from the concentration-response curve generated for each test compound.

*Aspergillus fumigatus* Infection of Human Alveoli Bilayers

In vitro models of human alveoli, consisting of a bilayer of human alveolar epithelial cells and endothelial cells, were prepared as previously described (Hope et al., 2007). This system allows administration of a test compound to the upper ("air" space) and/or lower ("systemic" space) compartments. This flexibility has been exploited to explore the effects of combination treatment by dosing Compound (I) to the upper chamber and posaconazole or other anti-fungal agents to the lower chamber. Primary human pulmonary artery endothelial cells (HPAEC) were harvested and diluted to $10^6$ cells/mL in EGM-2 media (Lonza, Basel, Switzerland). Transwells were inverted and the cell suspension (100 μL/well) applied to the base of each transwell. The inverted transwells were incubated at RT within a flow hood for 2 hr after which they were turned upright. EGM-2 media was added to the lower (700 μL/well) and upper (100 μL/well) compartments and the transwells were incubated for 48 hr (37° C., 5% $CO_2$). The EGM-2 media in the lower compartment was then replaced with fresh EGM-2 media. A549 cells were harvested and diluted to $5\times10^5$ cells/mL in 10% EBM, then added to the upper compartment (100 μL/well) of all transwells and the plates incubated for 72 hr (37° C., 5% $CO_2$). Conidia of itraconazole sensitive *Aspergillus fumigatus* s (NCPF2010) and itraconazole resistant (TR34-L98H) strains were cultured separately in Sabouraud dextrose agar for 3 days. A stock conidia suspension of either strain was prepared from a Sabouraud dextrose agar culture by washing with PBS-tween (10 mL; PBS containing 0.05% Tween-20, 100 U/mL Penicillin and 100 U/mL Streptomycin). The conidia count was assessed using a Neubauer haemocytometer and adjusted to $10^6$ conidia/mL with PBS. A working stock of conidia was prepared in EBM ($10^5$ conidia/mL) immediately prior to use.

Test and reference compounds (or neat DMSO as the vehicle) were added to the appropriate wells of 24-well plates (3 μL/well containing 600 μL of 2% FBS EBM) for lower compartment treatment and to 96-well plates (1 μL/well containing 200 μL of EBM [no FBS]) for the treatment of the upper compartment, to provide a final DMSO concentration of 0.5%. The media in the upper compartment was aspirated and that containing the appropriate test and reference compounds, or vehicle, were added (100 μL/well). Transwells were then transferred into the 24-well plate containing the test and reference compounds or DMSO vehicle. After incubation for 1 hr (35° C., 5% $CO_2$) the conidia suspension (10 μL/well) was added to the upper compartment of each transwell. Plates were then incubated for 24 hr (35° C., 5% $CO_2$). Supernatants from each compartment (5 μL/compartment) were collected and stored (−20° C.). Media was replaced daily after collection of the supernatants and all wells were treated with test and reference compounds or with DMSO, as described above, for 3 days. Samples continued to be collected until fungal growth was visible by eye in all transwells. The levels of GM in the supernatant in lower compartment were then measured by ELISA (BioRad, Calif., USA) as an index of *Aspergillus fumigatus* invasion.

Cell Viability: Resazurin Assay

BEAS2B cells were seeded in 384-well plates (100 μL; 3000/well/; BD Falcon, Catalogue No 353962) in RPMI-LHC8 (RPMI-1640 and LHC8 media combined in equal proportions) one day before experimentation. For cell-free control wells, RPMI-LHC8 (100 μL) was added. Test compounds (0.5 μL of a DMSO solution) were added to give a final DMSO concentration of 0.5% using an Integra VIA-FLO 96 (Integra, Zizers, Switzerland). BEAS2B cells were incubated with each test compound for 1 day (37° C./5% $CO_2$ in RPMI-LHC8). After addition of resazurin stock solution (5 μL, 0.04%) the plates were incubated for a further 4 hr (37° C./5% $CO_2$). The fluorescence of each well at 545 nm (excitation) and 590 nm (emission) was determined using a multi-scanner (Clariostar: BMG Labtech). The percentage loss of cell viability was calculated for each well relative to vehicle (0.5% DMSO) treatment. Where appropriate, a $CC_{50}$ value was calculated from the concentration-response curve generated from the concentration-response curve for each test compound.

In Vivo Anti-fungal Activity

*Aspergillus fumigatus* (ATCC 13073 [strain: NIH 5233], American Type Culture Collection, Manassas, Va., USA) was grown on Malt agar (Nissui Pharmaceutical, Tokyo, Japan) plates for 6-7 days at RT (24±1° C.). Spores were aseptically dislodged from the agar plates and suspended in sterile distilled water with 0.05% Tween 80 and 0.1% agar. On the day of infection, spore counts were assessed by haemocytometer and the inoculum was adjusted to obtain a concentration of $1.67\times10^8$ spores $mL^{-1}$ of physiological saline. To induce immunosuppression and neutropenia, A/J mice (males, 5 weeks old) were dosed with hydrocortisone (Sigma H4881; 125 mg/kg, sc,) on days 3, 2 and 1 before infection, and with cyclophosphamide (Sigma C0768; 250 mg/kg, i.p.) 2 days before infection. On day 0, animals were infected with the spore suspension (30 μL intra-nasally).

Test substances were administered intra-nasally (35 μL of a suspension (0.0032-10.0 mg/mL of drug substance in physiological saline) once daily, on days 1, 2 and 3 only (thereby representing a therapeutic treatment regimen). For extended prophylactic treatment, test compounds (35 μL of a suspension of 0.0032 or 0.016 mg/mL in physiological saline) were administered intra-nasally once daily for seven days. One group was dosed 30 min before infection on day 0 but not subsequently, while a second group was further dosed on days 1, 2 and 3 after infection. The effects of these treatment paradigms were compared with those obtained when treatment was restricted in other groups to either one day or 30 min before inoculation and then on days 1, 2 and 3 post infection in both cases. In a final group, dosing was limited still further with animals dosed twice, one day and 30 min before infection only.

Animal body weights were monitored daily and at 6 hr after the last dose of drug was administered on day 3, the animals were anesthetised, the tracheas cannulated and BALF blood and lung tissue were collected. The levels of IL-6 and TNFα in serum were determined using Quantikine® mouse IL-6 or TNF-α ELISA kit (R&D systems, Inc., Minneapolis, Minn., USA) respectively. *Aspergillus* GM in serum was determination using Platelia GM-EIA kits (Bio-Rad Laboratories, Redmond, Wash., USA). Cut-off index (COI) was calculated by the formula: Cut-off index=OD in sample/OD in cut-off control provided in kit. For tissue fungal load assays, 100 mg of lung tissue was removed aseptically and homogenized in 0.2 mL of 0.1% agar in sterile distilled water. Serially diluted lung homogenates were plated on Malt agar plates (50 μL/plate), and incubated at 24±1° C. for 72 to 96 hr. The colonies of *A. fumigatus* on each plate were counted and the fungal titre presented herein as CFUs per gram of lung tissue.

For determination of *Aspergillus fumigatus* DNA content, DNA was extracted from either infected lungs or *Aspergillus fumigatus* with the Isoplant (Nippon Gene) according to the manufacture's instruction. The tissues cut to <3 mm in any length were mixed with solution I (extraction buffer: 300 μL). Solution II (lysis buffer; benzyl chloride: 150 μL) was then added to the mixtures followed by mixing with a vortex mixer for 5 seconds. After incubation at 50° C. for 15 min, solution III (sodium acetate, pH5.2: 150 μL) was added the mixtures agitated vigorously for 1-3 seconds and then incubated on ice for 15 min. After the incubation, the mixtures were centrifuged at 12,000 g for 15 min at 4° C. DNA in the upper aq phases of the supernatants was precipitated with 100% ethanol (×2.5 vol), washed with 70% ethanol and dissolved in 5-10 μL of TE buffer.

DNA amplification was performed with Premix Ex Taq™ (Takara Bio) in the 96-well optical reaction plate. *Aspergillus fumigatus* 18S rRNA gene fragments were amplified with the primer pair; 5'-GGCCCTTAAATAGCCCGGT-3' (SEQ ID No. 1) and 5'-TGAGCCGATAGTCCCCCTAA-3' (SEQ ID No. 2), and hybridization probe; 5'-FAM-AGC-CAGCGGCCCGCAAATG-TAMRA-3' (SEQ ID No. 3). Real time PCR was performed in a reaction solution (25 μL) contained 50 ng of mouse lung DNA with 200 nM of probe) under the following conditions: initial incubation for 2 min at 50° C., initial denaturation for 10 min at 95° C., followed by 55 cycles of 15 seconds at 95° C. and 1 min at 65° C. The amounts of *Aspergillus fumigatus* DNA in 50 ng of mice lung DNA was evaluated from the standard curve with 0.05-50,000 pg of DNA from *Aspergillus fumigatus*.

Summary of Screening Results

Compound (I) exhibits potent inhibitory activity against planktonic fungal growth as evaluated in a broth microdilution assay (Table 3).

TABLE 3

The Effects of Treatment with Voriconazole, Posaconazole, Amphotericin B and Compounds (Ia-d)) on planktonic fungal growth of isolates of *Aspergillus fumigatus*.

| Treatment (Test Compound) | MIC$_{75}$ Values (nM) against the indicted *Aspergillus fumigatus* isolates[1] | | | | |
|---|---|---|---|---|---|
| | NCPF2010 | L98H | TR46 | NCPF7099 | NCPF7100 |
| Voriconazole | 511 | 2585 | >2860 | 113 | 543 |
| Posaconazole | 10.9 | 98.3 | 414 | 167 | 59.7 |
| Amphotericin B | 407 | 195 | 187 | 248 | 523 |
| Compound (Ia) | 2.81 | 12.7 | 93 | 10.0 | 12.7 |
| Compound (Ib) | 8.02 | 303 | 334 | 86.2 | 87.3 |
| Compound (Ic) | 2.27 | 54.9 | 164 | 11.5 | 10.9 |
| Compound (Id) | 8.51 | 70.0 | 316 | 11.7 | 25.2 |

Table Footnotes:

[1]Broth microdilution assay, n = 2-3.

In these assays, Compound (Ia) in particular showed significantly greater potency versus both the posaconazole-resistant strains (NCPF7099, NCPF7100, TR34/L98H and TR46/Y121F/T289A), as well as the posaconazole-sensitive strain (NCPF2010), than did posaconazole, voriconazole and Amphotericin B.

Compounds (Ia and Ic) also demonstrate potent inhibitory activity against fungal infection of bronchial epithelial cells (Table 4). In this assay system Compounds (Ia and Ic) showed significantly greater potency than voriconazole, and greater potency than posaconazole. Incubation with Compounds (Ia, Ib, Ic and Id) had no or little effect on the viability of BEAS2B bronchial epithelial cells at concentrations indicated below.

TABLE 4

The Effects of Treatment with Voriconazole, Posaconazole, Amphotericin B and Compounds (Ia-d) on *Aspergillus fumigatus* (NCPF2010) planktonic fungal growth, on fungal infection of BEAS2B bronchial epithelial cells and on BEAS2B cell viability.

| Treatment (Test Compound) | MIC$_{50}$/CC$_{50}$ Values for treatment indicated (nM) | |
|---|---|---|
| | Infection of BEAS2B cells[1] MIC$_{50}$ | BEAS2B Cell Viability[2] CC$_{50}$ |
| Voriconazole | 154 | >28600 |
| Posaconazole | 11.6 | >14300 |
| Amphotericin B | nt | 2343 |
| Compound (Ia) | 6.35 | >14600 |
| Compound (Ib) | nt | >14600 |
| Compound (Ic) | 1.86 | >14600 |
| Compound (Id) | nt | >14600 |

Table Footnotes:

[1]Bronchial epithelial cells; n = 1-3;

[2]n = 3;

nt: not tested.

The effects of Compound (I) on the growth of a wide range of fungal pathogens was evaluated using the CLSI broth microdilution methods. Compound (Ia) was found to be a potent inhibitor of the growth of *Aureobasidium pullulans, Rhizopus oryzae, Cryptococcus neoformans, Chaetomimum globosum, Penicillium chrysogenum, Fusarium graminerarum* (*Gibberella zeae*), *Cladosporium herbarum* and *Trichophyton rubrum* as well as some *Candida* spp. (notably *Candida albicans, Candida glabrata* and *Candida krusei*) and some *Aspergillus* spp. (notably *Aspergillus flavus*) (Table 5).

TABLE 5

The inhibitory effects of Compound (Ia) on the growth of a range of fungal species.

| Fungal Agent | Strain | Compound (Ia) MIC$_{50}$ (µg/mL) | Compound (Ia) MIC$_{100}$ (µg/mL) | Voriconazole MIC$_{50}$ (µg/mL) | Voriconazole MIC$_{100}$ (µg/mL) | Posaconazole MIC$_{50}$ (µg/mL) | Posaconazole MIC$_{100}$ (µg/mL) |
|---|---|---|---|---|---|---|---|
| Aspergillus flavus | ATCC204304 | 0.13 | 0.13 | 1.0 | 2.0 | 0.063 | 0.13 |
| Aureobasidium pullulans | ATCC9348 | 0.25 | 1.0 | >8.0 | >8.0 | 0.25 | 1.0 |
| Candida albicans | 20240.047 | 0.016 | >2.0 | 0.031 | >8.0 | 0.031 | >8.0 |
| | ATCC10231 | 0.25 | >2.0 | 0.25 | >8.0 | 0.13 | >8.0 |
| | 20183.073 | 0.125 | >2.0 | 4.0 | >8.0 | 0.25 | >8.0 |
| Candida glabrata | ATCC36583 | 0.25 | >2.0 | 0.25 | >8.0 | 0.5 | >8.0 |
| | 20197.1 | 0.0078 | >2.0 | 0.031 | >8.0 | 0.031 | >8.0 |
| Candida krusei | ATCC6258 | 0.25 | 0.25 | 0.25 | 1.0 | 0.13 | 0.25 |
| Rhizopus oryzae | ATCC11145 | 0.25 | 0.5 | 8.0 | >8.0 | 0.13 | >8.0 |
| Cryptococcus neoformans | ATCC24067 | 0.016 | 0.063 | 0.016 | 1.0 | 0.016 | 0.25 |
| Chaectomium globosum | ATCC44699 | 0.031 | 0.13 | 0.5 | 1.0 | 0.13 | 0.25 |
| Fusarium graminerarum | ATCC16106 | 0.13 | 0.5 | >8.0 | >8.0 | >8.0 | >8.0 |
| Penicillium chrysogenum | ATCC9480 | 0.063 | 0.13 | 1.0 | 2.0 | 0.063 | 0.13 |
| Cladosporium herbarum | NCPF2564 | 0.016 | 0.016 | ND | ND | ND | ND |
| Trichophyton rubrum | ATCC10218 | ND | 0.031 | <0.008 | 0.063 | <0.008 | 0.031 |

Table footnotes:
MIC$_{50}$/MIC$_{100}$ = concentration required for 50% and 100% inhibition of fungal growth by visual inspection (CLSI).
ND: not determined Inhibitory activities on alveolar invasion of *Aspergillus fumigatus* (azole sensitive strain: NCPF2010; and azole resistant strain TR34/L98H) were determined by measuring galactomannan (GM) in the bottom chamber of human alveoli bilayers 1 day post infection. Administration of Compound (Ia) to the apical chamber produced concentration-dependent inhibition of GM levels in the bottom chamber, with maximum effects exceeding 90% for both strains (Tables 6 and 7).

TABLE 6

Effects of Compound (Ia) and Posaconazole on the invasion of *Aspergillus fumigatus* (azole susceptible strain: NCPF2010) into the lower chamber in human alveoli bilayers (transwells).

| Treatment (Test Compound) | MIC Values for treatment indicated (nM) | |
|---|---|---|
| | MIC$_{50}$ | MIC$_{90}$ |
| Posaconazole | 155 | 212 |
| Compound (Ia) | 154 | 185 |

Table Footnote:
n = 3.

TABLE 7

Effects of Compound (Ia) and Posaconazole on the invasion of *Aspergillus fumigatus* (azole resistant strain: TR34/L98H) into the lower chamber in human alveoli bilayers (transwells).

| Treatment Test Compound | MIC Values for treatment indicated (nM) | |
|---|---|---|
| | MIC$_{50}$ | MIC$_{90}$ |
| Posaconazole | 315 | 793 |
| Compound (Ia) | 261 | 417 |

Table Footnote:
n = 1

When the inhibitory activities were monitored for several days post infection, the early inhibitory effects of monotherapy with either Compound (Ia) (0.1 µg/mL in the upper chamber) or posaconazole (0.01 µg/mL in the lower chamber) were found to disappear rapidly (Table 8). In contrast, the combined treatment with Compound (Ia) in the upper chamber and posaconazole in the lower chamber (as above) led to sustained inhibition of invasion post infection. Consequently, the DFB$_{50}$ for the combination treatment was 3.63 days, much longer than the values for either compound alone (Table 8). This synergistic or at least additive effect of combination therapy also occurred when treatment with Compound (Ia) was combined with that of itraconazole, voriconazole or caspofungin (results not shown).

TABLE 8

Effects of Compound (Ia), Posaconazole and the treatment combination on *Aspergillus fumigatus* (NCPF2010) invasion into the lower chamber in human alveoli bilayers (transwells).

GM Levels in the Lower Chamber for Treatments Indicated OD value (% inhibition vs. control)

| Treatment Day | Vehicle | Compound (Ia)[1] Upper Chamber | Posaconazole[2] Lower Chamber | Combination Treatment |
|---|---|---|---|---|
| 0 | 0 | 0 | 0 | 0 |
| 1 | 0.73 | 0.24 (66) | 0.074 (89) | 0.019 (97) |
| 2 | 1.73 | 1.71 (1.5) | 1.71 (1.5) | 0.11 (94) |
| 3 | 1.82 | 1.67 (8.6) | 1.70 (7.1) | 0.18 (90) |
| 4 | 1.65 | 1.68 (−1.6) | 1.70 (−3.0) | 1.34 (19) |
| 5 | 1.64 | 1.63 (0.2) | 1.69 (−3.6) | 1.72 (−5.3) |
| 6 | 1.55 | 1.57 (−1.8) | 1.59 (−3.0) | 1.62 (−4.6) |
| 7 | 1.66 | 1.54 (7.1) | 1.62 (2.5) | 1.59 (4.4) |
| DFB$_{50}$ Values for treatments indicated | | 1.04 | 1.16 | 3.63 |

Table footnotes:
[1]Dosed at 0.1 μg/mL;
[2]Dosed at 0.01 μg/mL;
DFB$_{50}$: Days taken to reach a fungal burden of 50% of control In addition, this combination treatment has been tested in bilayers infected with the azole resistant strain of *Aspergillus fumigatus*: TR34-L98H (Table 9). Monotherapy with Compound (Ia) (0.3 μg/mL) in the upper chamber or with posaconazole (0.1 μg/mL) in the lower chamber showed limited benefit. In contrast, the combination of Compound (Ia) and posaconazole showed marked inhibitory effects on fungal invasion into the lower chamber.

TABLE 9

Effects of Compound (Ia), Posaconazole and the treatment combination on *Aspergillus fumigatus* (azole resistant strain: TR34-L98H) invasion into the lower chamber in the alveolar bilayer cell system (transwells).

GM Levels in the Lower Chamber for Treatments Indicated OD value (% inhibition vs. vehicle control)

| Treatment Day | Vehicle | Compound (I)[1] Upper Chamber | Posaconazole[2] Lower Chamber | Combination Treatment |
|---|---|---|---|---|
| 0 | 0 | 0 | 0 | 0 |
| 1 | 0.63 | 0.016 (98) | 0.016 (98) | 0.014 (98) |
| 2 | 1.11 | 0.84 (24) | 0.73 (35) | 0.015 (99) |
| 3 | 1.06 | 1.01 (4.6) | 1.16 (−10) | 0.020 (98) |
| DFB$_{50}$ Values for treatments indicated | | 1.53 | 1.94 | >3 |

Table footnotes:
[1]Dosed at 0.3 μg/mL;
[2]Dosed at 0.1 μg/mL;
DFB$_{50}$: Days taken to reach a fungal burden of 50% of control When given intranasally to immunocompromised, neutropenic mice, on days 1, 2 and 3 following inoculation (therapeutic treatment), Compound (Ia) showed some protection against body weight loss, measured over 3 days, caused by infection with *Aspergillus fumigatus* at lower doses than were required of posaconazole (Table 10).

TABLE 10

The Effects of Treatment with Compound (Ia) or Posaconazole on the body weight loss of immunocompromised, neutropenic mice, caused by *Aspergillus fumigatus* infection.

| Treatment Regimen[2] | Drug Conc (mg/mL) | Body weight loss[1,2] (% Inhibition of weight loss) | |
|---|---|---|---|
| | | Day 2 | Day 3 |
| Vehicle plus Spores | none | 5.5 ± 1.5 | 10.7 ± 1.8 |
| Compound (Ia) | 0.0032 | 4.2 ± 1.2 (24) | 9.7 ± 2.1 (9) |
| | 0.016 | 3.6 ± 1.2 (35) | 9.7 ± 3.2 (9) |
| | 0.08 | 2.8 ± 2.4 (49) | 8.3 ± 6.7 (22) |
| Vehicle plus Spores | none | 4.7 ± 2.1 | 9.3 ± 2.7 |
| Posaconazole | 0.4 | 5.4 ± 0.4 (−15) | 9.2 ± 4.0 (1) |
| | 2 | 3.9 ± 1.3 (17) | 7.1 ± 1.9 (24) |
| | 10 | 3.9 ± 1.3 (17) | 4.3 ± 1.8 (54) |

Table Footnotes:
[1]% weight loss caused by infection with Aspergillus fumigatus compared with animal weight on day 1 when treatment was started;
[2]Two separate studies conducted.

Furthermore, therapeutic treatment with Compound (Ia), showed superior effects to posaconazole on fungal load in the lung, on galactomannan concentrations in serum and *Aspergillus fumigatus* DNA content in lungs. These data for Compound (I) are shown in Table 11 and FIGS. 1, 2 and 3.

TABLE 11

The Effects of Prophylactic and Therapeutic Treatment with Compound (Ia) on CFU in lung, on galactomannan concentrations in serum and on *Aspergillus* DNA in the lungs of *Aspergillus fumigatus* infected, immuno-compromised, neutropenic mice.

| Treatment Regimen | Drug Conc (μg/mL) | % Inhibition of response | | |
|---|---|---|---|---|
| | | CFU (/mg of lung) | GM in serum (COI) | DNA in Lung (pg/50 ng mouse DNA) |
| Vehicle plus Spores | None | 31.7 ± 17.4 | 3.38 ± 2.02 | 70.7 ± 41.3 |
| Compound (Ia) | 3.2 | 25.8 ± 20.8 (19) | 2.85 ± 2.76 (16) | 41.7 ± 29.0 (41) |
| | 16 | 24.2 ± 15.8 (24) | 3.01 ± 2.14 (11) | 56.1 ± 53.4 (21) |
| | 80 | 9.30 ± 5.20 (71) | 0.53 ± 0.38 (84) | 4.10 ± 4.60 (94) |

Table Footnotes:
The data for fungal load are shown as the mean ± standard error of the mean (SEM; n = 6).

The ID$_{50}$ values for posaconazole and Compound (Ia), administered therapeutically in independent experiments, are also presented below (Table 12).

TABLE 12

ID$_{50}$ values for Therapeutic Treatment with Posaconazole and Compound (Ia) on fungal load in the lung on galactomannan concentrations in serum and on *Aspergillus fumigatus* DNA content in lung tissue, in *Aspergillus fumigatus* infected, immuno-compromised, neutropenic mice.

| Drug substance (Therapeutic Regimen) | ID$_{50}$ Values for response indicated (mg/mL) | | |
|---|---|---|---|
| | Lung Fungal Load | GM in serum | *A. fumigatus* DNA in Lung |
| Compound (Ia) | 0.051 | 0.047 | 0.050 |
| Posaconazole | 0.39 | 0.59 | Nt |

Table Footnotes:
nt: not tested

Figure 2:
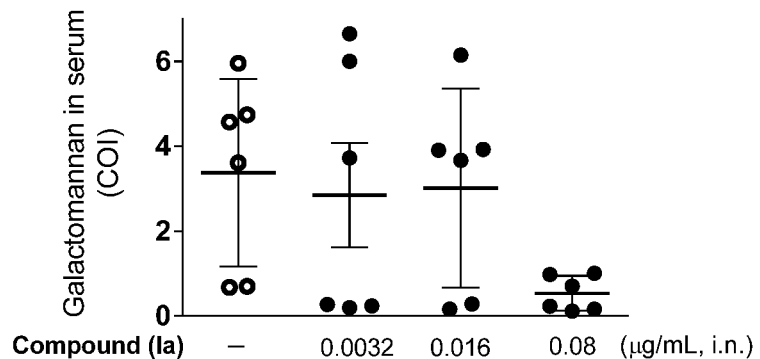
FIG. 2 shows the effects of therapeutic treatment with Compound (Ia) on serum galactomannan concentrations in *Aspergillus fumigatus* infected, immuno-compromised, neutropenic mice.
Figure 3:
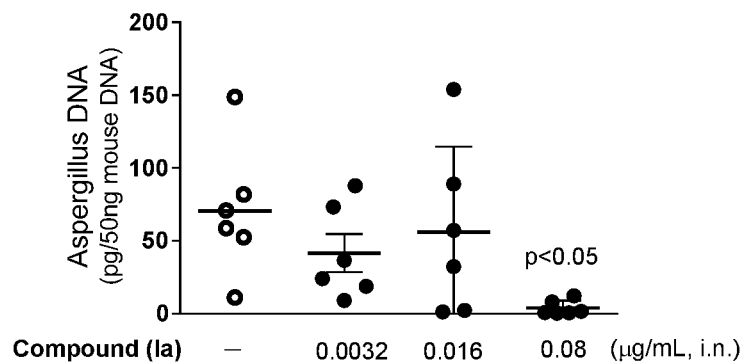
FIG. 3 shows the effects of therapeutic treatment with Compound (Ia) on *Aspergillus fumigatus* DNA content in the lungs of *Aspergillus fumigatus* infected, immuno-compromised, neutropenic mice.

Therapeutic treatment with Compound (Ia) was also found to inhibit serum cytokine concentrations in *Aspergil-* lus fumigatus infected, immunocompromised, neutropenic mice. (Tables 13 and 14; FIGS. 1, 2 and 3). The calculated $ID_{50}$ values for inhibition of serum cytokine levels (Table 14) are very similar to those observed for lung fungal load, serum galactomannan concentrations and for lung *Aspergillus fumigatus* DNA content (above).

dosing since seven days of prophylaxis produced greater anti-fungal effects than did prophylactic treatment for a single day. The compound's persistence of action in the lung is suggested by the finding that treatment on days −7 to day 0 generated superior anti-fungal effects on day 3 than those resulting from treatment on days −1 and 0, only.

TABLE 15

Effects of extended prophylactic dosing of Compound (Ia) on fungal load (CFU) in lung and on GM concentrations in BALF and serum in *Aspergillus fumigatus* infected, immuno-compromised, neutropenic mice.

| Treatment Regimen[1] (Days dosed) | Dose of Compound (Ia) (µg/mL) | CFU values, COI values for GM in BALF and serum and % Inhibition of responses[2] | | |
|---|---|---|---|---|
| | | CFU (/mg of lung) | GM in BALF (COI) | GM in Serum (COI) |
| Vehicle plus Spores | None | 9.2 ± 4.9 | 4.1 ± 0.7 | 3.9 ± 0.7 |
| −7 to +3 | 0.64 | 2.0 ± 3.6 (78) | 3.1 ± 0.85 (24) | 2.6 ± 0.82 (33) |
| −1 to +3 | 0.64 | 4.0 ± 5.2 (57) | 3.9 ± 0.59 (5) | 3.6 ± 0.52 (8) |
| −7 to +3 | 3.2 | 0.04 ± 0.08 (99.6) | 1.5 ± 0.59 (63) | 1.5 ± 0.85 (62) |
| −1 to +3 | 3.2 | 1.0 ± 1.4 (89) | 3.4 ± 0.46 (17) | 2.8 ± 0.24 (28) |
| −7 to 0 | 3.2 | 0.9 ± 1.1 (90) | 2.9 ± 0.97 (29) | 2.6 ± 0.48 (33) |
| −1, 0 | 3.2 | 20.4 ± 15.7 (−222) | 4.5 ± 0.63 (−10) | 4.7 ± 0.65 (−21) |

Table footnotes:
[1]The N value was five for all vehicle and drug treated groups;
[2]The data for fungal load and GM levels are shown as the mean ± standard error of the mean and the percentage inhibition, with respect to vehicle.

TABLE 13

The Effects of Therapeutic Treatment with Compound (Ia) on IL-6 and TNFα levels in the serum of *Aspergillus fumigatus* infected, immunocompromised, neutropenic mice.

| Treatment Regimen | Drug Conc (µg/mL) | Conc of Biomarkers (pg/mL) (% Inhibition) | |
|---|---|---|---|
| | | IL-6 | TNFα |
| Vehicle plus Spores | none | 298 ± 142 | 35.3 ± 10.1 |
| Compound (Ia) | 3.2 | 247 ± 185 (17) | 28.1 ± 13.8 (20) |
| | 16 | 262 ± 185 (12) | 21.8 ± 14.6 (38) |
| | 80 | 66.5 ± 32.9 (78) | 4.7 ± 1.0 (87) |

Table Footnotes:
The data for biomarker concentrations are shown as the mean ± standard error of the mean (SEM), N = 6.

TABLE 14

$ID_{50}$ values for Therapeutic Treatment with Compound (Ia) on IL-6 and TNFα levels in serum in *Aspergillus fumigatus* infected, immuno-compromised, neutropenic mice.

| Drug substance (Prophylactic Regimen) | $ID_{50}$ Values for biomarkers indicated (mg/mL) | |
|---|---|---|
| | IL-6 | TNFα |
| Compound (Ia) | 0.050 | 0.027 |

The effects of extended prophylactic dosing with Compound (Ia) in *Aspergillus fumigatus* infected, immuno-compromised, neutropenic mice were also evaluated. Extended prophylaxis with Compound (Ia) was found to inhibit fungal load in the lung, as well as GM concentrations in both BALF and serum, at 25 fold lower doses than those used in a previous study (Table 15). Furthermore, the data suggest an accumulation of anti-fungal effects in the lung on repeat dosing since seven days of prophylaxis produced greater anti-fungal effects than did prophylactic treatment for a single day. The compound's persistence of action in the lung is suggested by the finding that treatment on days −7 to day 0 generated superior anti-fungal effects on day 3 than those resulting from treatment on days −1 and 0, only.

In Vivo Pharmacokinetics

It is a commonly used procedure for pulmonary, therapeutic agents to be dosed into the lungs of animals, for example mice, and plasma collected at various time points after dosing in order to characterise the resulting systemic exposure to the administered compound.

The compound of the invention may be tested in such above mentioned in vivo systems.

Summary of the Biological Profile of Compound (I)

Compound (I) in the form of all four stereoisomers has been found to be a potent inhibitor of *Aspergillus fumigatus* planktonic growth and bronchial epithelial cell infection. Compound (Ia) inhibited the growth of posaconazole-resistant and voriconazole-resistant *Aspergillus fumigatus* isolates, demonstrating greater potency than posaconazole, voriconazole and Amphotericin B against these strains. A wide range of other pathogenic fungi were also found to be sensitive to Compound (Ia). Synergistic or at least additive effects have been shown for Compound (Ia) in combination with posaconazole, itraconazole, voriconazole and caspofungin. In vivo, in *Aspergillus fumigatus* infected, immunocompromised, neutropenic mice, Compound (Ia), demonstrated potent inhibition of *Aspergillus fumigatus* infection, as well as the associated lung immune response when dosed therapeutically or prophylactically. Compound (Ia) was also efficacious in reducing infection-dependent body weight loss. These inhibitory effects were superior to those of posaconazole. It is clinically significant that the beneficial anti-fungal effects of Compound (I) are observed in a therapeutic setting.

REFERENCES

Agbetile, J., Fairs, A., Desai, D., Hargadon, B., Bourne, M., Mutalithas, K., Edwards, R., Morley, J. P., Monteiro, W.

R., Kulkarni, N. S., Green, R H, Pavord, I. D., Bradding, P., Brightling, C. E., Wardlaw, A. J. and Pashley, C. H. Isolation of filamentous fungi from sputum in asthma is associated with reduced post-bronchodilator FEV1. *Clin. Exp. Allergy,* 2012, 42, 782-91.

Bafadhel M., McKenna S., Aqbetile J., Fairs A., Desai D., Mistry V., Morley J. P., Pancholi M., Pavord I. D., Wardlaw A. J., Pashley C. H. and Brightling C. E. *Aspergillus fumigatus* during stable state and exacerbations of COPD. *Eur. Respir. J.,* 2014, 43, 64-71.

Bowyer P. and Denning D. W. Environmental fungicides and triazole resistance in *Aspergillus. Pest Management Science,* 2014, 70, 173-178.

Chishimba L., Niven R. M., Fom M., Cooley J. and Denning D. W. Voriconazole and Posaconazole Improve Asthma Severity in Allergic Bronchopulmonary Aspergillosis and Severe Asthma with Fungal Sensitization. *Pharmacotherapy,* 2012, 49, 423-433.

Chotirmall S. H., O'Donoghue E., Bennett K., Gunaratnam C., O'Neill S. J. and McElvaney N. G. Sputum *Candida albicans* presages $FEV_1$ decline and hospital-treated exacerbations in cystic fibrosis. *Chest,* 2010, 138, 1186-95.

CLSI M27-A2: Reference method for broth dilution antifungal susceptibility testing of yeasts; Approved standard, 2nd ed, NCCLS document M27-A2, Clinical and Laboratory Standards Institute, Wayne, Pa., 2002.

CLSI M38-A2: Reference method for broth dilution antifungal susceptibility testing of filamentous fungi; Approved standard, 2nd ed, CLSI document M38-A2, Clinical and Laboratory Standards Institute, Wayne, Pa., 2008.

Denning D. W., Pleuvry A. and Cole D. C. Global burden of chronic pulmonary aspergillosis as a sequel to pulmonary tuberculosis. *Bull. World Health Organ.,* 2011a, 89, 864-872.

Denning D. W., Park S., Lass-Flori C., Fraczek M. G., Kirwan M., Gore R., Smith J., Bueid A., Moore C. B., Bowyer P. and Perlin D. S. High frequency triazole resistance found in nonculturable *Aspergillus fumigatus* from lungs of patients with chronic fungal disease. *Clin. Infect. Dis.,* 2011b, 52, 1123-1129.

Dimopoulos G., Frantzeskaki F., Poulakou G. and Armaganidis A. Invasive aspergillosis in the intensive care unit. *Ann. NY Acad. Sci.,* 2012, 1272, 31-39.

Geist M. J. P., Egerer G., Burhenne J., Riedel K-D. and Mikus G. Induction of voriconazole metabolism by rifampin in a patient with acute myeloid leukemia: importance of interdisciplinary communication to prevent treatment errors with complex medications. *Antimicrob. Agents Chemother.,* 2007, 51, 3455-3456.

Hope W. W., Kruhlak M. J., Lyman C. A., Petraitiene R., Petraitis V., Francesconi A., Kasai M., Mickiene D., Sein T., Peter J., Kelaher A. M., Hughes J. E., Cotton M. P., Cotten C. J., Bacher J., Tripathi S., Bermudez L., Maugel T. K., Zerfas P. M., Wingard J. R., Drusano G. L. and Walsh T. J. Pathogenesis of *Aspergillus fumigatus* and the kinetics of galactomannan in an in vitro model of early invasive pulmonary aspergillosis: implications for antifungal therapy. *J. Infect. Dis.,* 2007, 195(3), 455-466.

Jeong S., Nguyen P. D. and Desta Z. Comprehensive in vitro analysis of voriconazole inhibition of eight cytochrome P450 (CYP) enzymes: major effect on CYPs 2B6, 2C9, 2C19, and 3A. *Antimcrob. Agents Chemother.,* 2009, 53, 541-551.

Kaur S. and Singh S. Biofilm formation by *Aspergillus fumigatus. Med. Mycol.,* 2014, 52, 2-9.

Kimura G., Ueda K., Eto S., Watanabe Y., Masuko T., Kusama T., Barnes P. J., Ito K. and Kizawa Y. Toll-like receptor 3 stimulation causes corticosteroid-refractory airway neutrophilia and hyper-responsiveness in mice. *Chest.* 2013, 144, 99-105.

Lat A. and Thompson G. R. Update on the optimal use of voriconazole for invasive fungal infections. *Infect. Drug Resist.,* 2011, 4, 43-53.

Limper A. H., Knox K. S., Sarosi G. A., Ampel N. M., Bennett J. E., Catanzaro A., Davies S. F., Dismukes W. E., Hage C. A., Marr K. A., Mody C. H., Perfect J. R. and Stevens D. A. An Official American Thoracic Society Statement: Treatment of Fungal Infections in Adult Pulmonary and Critical Care Patients. *Am. J. Respir. Crit. Care Med.,* 2011, 183, 96-128.

Levin M-D., den Hollander J. G., van der Holt B., Rijnders B. J., van Vliet M., Sonneveld P. and van Schaik R. H. Hepatotoxicity of oral and intravenous voriconazole in relation to cytochrome P450 polymorphisms. *J. Antimicrob. Chemother.,* 2007, 60, 1104-1107.

Lin S-J, Scranz J and Teutsch S. M. *Aspergillus* case-fatality rate: systematic review of the literature. *Clin. Infect. Dis.,* 2001, 32, 358-366.

Monteiro M. C., de la Cruz M, Cantizani J., Moreno C., Tormo J. R., Mellado E, De Lucas J. R., Asensio F., Valiante V., Brakhage A. A., Latgé J P, Genilloud O., Vicente F. A new approach to drug discovery: high-throughput screening of microbial natural extracts against *Aspergillus fumigatus* using resazurin. *J. Biomol. Screen.* 2012, 17, 542-549.

Pasqualotto A. C., Powell G., Niven R. and Denning D. W. The effects of antifungal therapy on severe asthma with fungal sensitization and allergic bronchopulmonary aspergillosis. *Respirology,* 2009, 14, 1121-127.

Pierce C. G., Uppuluri P., Tristan A. R., Wormley F. L. Jr., Mowat E., Ramage G., Lopez-Ribot J. L. A simple and reproducible 96-well plate-based method for the formation of fungal biofilms and its application to antifungal susceptibility testing. *Nat. Protoc.,* 2008, 3, 1494-500.

Rankin, N. Disseminated aspergillosis and moniliasis associated with granulocytosis and antibiotic therapy. *Br. Med. J.,* 1953, 183, 918-9.

Rodriguez-Tudela J. L., Arendrup M. C., Arikan S., Barchiesi F., Bille J., Chyssanthou E., Cuenca-Estrella M., Dannaoui E., Denning D. W., Donnelly J. P., Fegeler W., Lass-Flörl C., Moore C., Richardson M., Gaustad P., Schmalreck A., Velegraki A. and Verweij P. Subcommittee of Antifungal Susceptibility Testing (AFST) of the ESCMID European Committee for Antimicrobial Susceptibility testing (EUCAST). EUCAST DEFINITIVE DOCUMENT E.DEF 9.1: Method for the determination of broth dilution minimum inhibitory concentrations of antifungal agents for conidia forming moulds. E.DEF 9.1 2008, 1-13.

Salmeron G., Porcher R., Bergeron A., Robin M., Peffault de Latour R., Ferry C., Rocha V., Petropoulou A., Xhaard A., Lacroix C., Sulahian A., Socié G., and Ribaud P. Persistent poor long-term prognosis of alogeneic hematopoietic stem cell transplant recipients surviving invasive aspergllosis. *Haematolologica,* 2012, 97, 1357-1363.

Shaus S. E., Larrow J. F. and Jacobsen E. N. Practical Synthesis of Enantiopure Cyclic 1,2-Amino Alcohols via Catalytic Asymmetric Ring Opening of Meso Epoxides. *J. Org. Chem.,* 1997, 62, 4197-4199.

Thompson G. R. and Patterson T. F. Pulmonary aspergillosis. *Seminars in Respiratory and Critical Care Medicine,* 2008, 29, 103-110.

Wexler D., Courtney R., Richards W., Banfield C., Lim J. and Laughlin M. Effect of posaconazole on cytochrome P450 enzymes: a randomized, open-label two-way crossover study. *Eur. J. Pharm. Sci.,* 2004, 21, 65-653.

The invention claimed is:

1. A process for preparing a compound of formula (I):

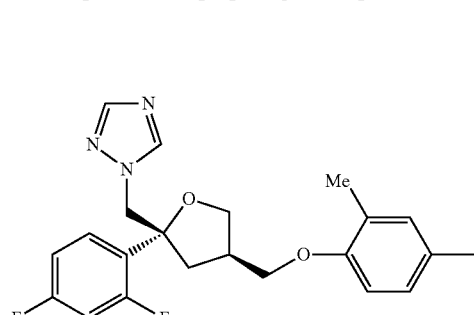

Compound (I)

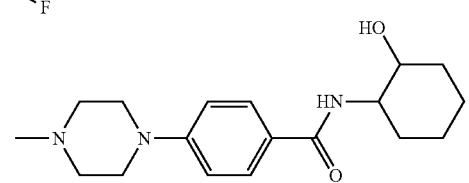

or a pharmaceutically acceptable salt thereof wherein the process comprises reacting a compound of formula (6):

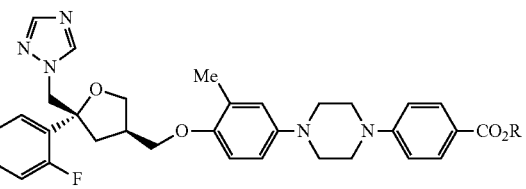

wherein R is H;
with 2-aminocyclohexanol or a salt thereof.

2. The process according to claim 1 wherein the compound of formula (I) is prepared in the form of a singular stereoisomer selected from compounds (Ia) and (Ib):

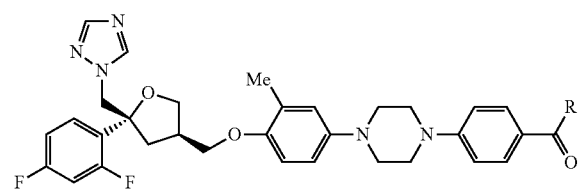

-continued
| R | Compound |
|---|---|
| 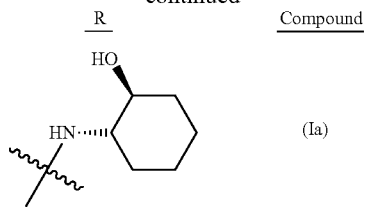 | (Ia) |
|  | (Ib) |
or a pharmaceutically acceptable salt of any one thereof.
3. The process according to claim 2 wherein the compound of formula (I) is compound (Ia):
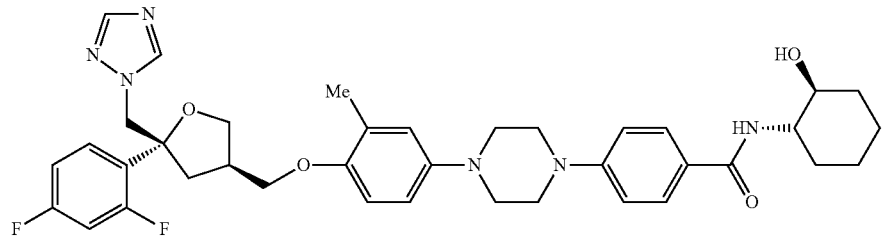
Compound (Ia)
or a pharmaceutically acceptable salt thereof.
* * * * *

SEQUENCE LISTING

<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: First primer

<400> SEQUENCE: 1
ggcccttaaa tagcccggt                                                19

<210> SEQ ID NO 2
<211> LENGTH: 20
<212> TYPE: DNA
<213> ORGANISM: Artificial Sequence
<220> FEATURE:
<223> OTHER INFORMATION: Second primer

<400> SEQUENCE: 2
tgagccgata gtcccctaa                                                20

<210> SEQ ID NO 3
<211> LENGTH: 19
<212> TYPE: DNA
<213> ORGANISM: Artificial Sequence
<220> FEATURE:
<223> OTHER INFORMATION: Hybridisation probe DNA region

<400> SEQUENCE: 3
agccagcggc ccgcaaatg                                                19